US010674919B2

(12) United States Patent
Banke

(10) Patent No.: US 10,674,919 B2
(45) Date of Patent: Jun. 9, 2020

(54) METHOD AND APPARATUS FOR TRANSDERMAL IN VIVO MEASUREMENT BY RAMAN SPECTROSCOPY

(71) Applicant: RSP SYSTEMS A/S, Odense S (DK)

(72) Inventor: Stefan Ovesen Banke, Nyborg (DK)

(73) Assignee: RSP SYSTEMS A/S, Odense S (DK)

( * ) Notice: Subject to any disclaimer, the term of this patent is extended or adjusted under 35 U.S.C. 154(b) by 50 days.

(21) Appl. No.: 15/508,580

(22) PCT Filed: Aug. 24, 2015

(86) PCT No.: PCT/EP2015/069332
§ 371 (c)(1),
(2) Date: Mar. 3, 2017

(87) PCT Pub. No.: WO2016/034448
PCT Pub. Date: Mar. 10, 2016

(65) Prior Publication Data
US 2017/0273564 A1 Sep. 28, 2017

(30) Foreign Application Priority Data

Sep. 4, 2014 (GB) .................................. 1415671.5

(51) Int. Cl.
A61B 5/00 (2006.01)
G01J 3/44 (2006.01)
(Continued)

(52) U.S. Cl.
CPC .......... A61B 5/0075 (2013.01); A61B 5/1455 (2013.01); A61B 5/7221 (2013.01);
(Continued)

(58) Field of Classification Search
CPC .................................................. A61B 5/0075
(Continued)

(56) References Cited

U.S. PATENT DOCUMENTS 6,352,502 B1 * 3/2002 Chaiken ............... A61B 5/0059
356/300
2002/0049389 A1 * 4/2002 Abreu .................. A61B 3/1241
600/558
(Continued)

FOREIGN PATENT DOCUMENTS

WO  WO 97/36540 A1  10/1997
WO  WO 00/02479 A1  1/2000
(Continued)

OTHER PUBLICATIONS

Caspers, P. J., et al., "Combined In Vivo Confocal Raman Spectroscopy and Confocal Microscopy of Human Skin," Biophysical Journal, vol. 85, Jul. 2003, pp. 572-580.
(Continued)

Primary Examiner — Tarifur R Chowdhury
Assistant Examiner — Omar H Nixon
(74) Attorney, Agent, or Firm — Pillsbury Winthrop Shaw Pittman LLP

(57) ABSTRACT

The use of a transdermal Raman spectrum to measure glucose or other substance concentration can give an inaccurate result if the Raman signals originate at a wrong skin depth. To predict whether a spectrum of Raman signals received transdermally in a confocal detector apparatus and having at least one component expected to have an intensity representing the concentration of glucose or another skin component at a point of origin of the Raman signals below the surface of the skin will accurately represent the concentration, peaks in the spectrum at 883/4 cm$^{-1}$ and 894 cm$^{-1}$ are measured to determine whether the Raman signals originate primarily within the stratum corneum so that the spectrum will be less likely to represent the concentration accurately or originate primarily below the stratum corneum (Continued)

so that the spectrum will be more likely to represent the concentration accurately.

25 Claims, 9 Drawing Sheets

(51) Int. Cl.
G01N 21/65 (2006.01)
G01J 3/02 (2006.01)
G01J 1/42 (2006.01)
A61B 5/1455 (2006.01)
A61B 5/145 (2006.01)

(52) U.S. Cl.
CPC .......... *G01J 1/4257* (2013.01); *G01J 3/0208* (2013.01); *G01J 3/0216* (2013.01); *G01J 3/44* (2013.01); *G01N 21/65* (2013.01); *A61B 5/14532* (2013.01); *A61B 5/14551* (2013.01)

(58) Field of Classification Search
USPC ........................................ 356/301
See application file for complete search history.

(56) References Cited

U.S. PATENT DOCUMENTS

| 2004/0024553 | A1* | 2/2004 | Monfre | A61B 5/14532 |
| | | | | 702/104 |
| 2005/0117150 | A1* | 6/2005 | Puppels | A61B 5/0059 |
| | | | | 356/301 |
| 2007/0035793 | A1* | 2/2007 | Hendriks | G02B 26/005 |
| | | | | 369/112.01 |
| 2007/0049809 | A1* | 3/2007 | Bechtel | A61B 5/14532 |
| | | | | 600/316 |
| 2014/0320855 | A1* | 10/2014 | Chen | G01N 21/65 |
| | | | | 356/301 |

FOREIGN PATENT DOCUMENTS

| WO | WO 01/39665 A2 | 6/2001 |
| WO | WO 2008/052221 A2 | 5/2008 |
| WO | WO 2009/002170 A1 | 12/2008 |
| WO | WO 2009/149266 A2 | 12/2009 |
| WO | WO 2010/114361 A1 | 10/2010 |
| WO | WO 2011/083111 A1 | 7/2011 |

OTHER PUBLICATIONS

Ermakov, I. V., et al., "Resonance Raman detection of carotenoid antioxidants in living human tissues," Optics Letters, vol. 26, No. 15, Aug. 2001, pp. 1179-1181.

Chaiken, J., et al., "Noninvasive blood analysis by tissue modulated NIR Raman spectroscopy," Visualization of Temporal and Spatial Data for Civilian and Defense Applications, Proceedings of the SPIE, vol. 4368, 2001, pp. 134-145.

Movasaghi, Z., et al., "Raman Spectroscopy of Biological Tissues," Applied Spectroscopy Reviews, vol. 42, (2007), ISSN: 0570-4928, pp. 493-541.

Olesberg, J. T., et al., "In Vivo Near-Infrared Spectroscopy of Rat Skin Tissue with Varying Blood Glucose Levels," Analytical Chemistry, vol. 78, No. 1, Jan. 2006, pp. 215-223.

Enejder, A. M. K., et al., "Raman spectroscopy for noninvasive glucose measurements," Journal of Biomedical Optics, vol. 10, No. 3, May/Jun. 2005, pp. 031114-1-031114-9.

Ryder, A. G., et al., "Quantitative analysis of cocaine in solid mixtures using Raman spectroscopy and chemometric methods," Journal of Raman Spectroscopy, vol. 31, (2000), pp. 221-227.

Fruhstorfer, H., et al., "Thickness of the Stratum Corneum of the Volar Fingertips," Clinical Anatomy, vol. 31, (2000), pp. 429-433.

Marks, J., et al., *Lookingbill and Marks' Principles of Dermatology* (Fourth Edition). Elsevier Inc., (2006), Chapter 2, p. 7, ISBN 1-4160-3185-5.

International Search Report as issued in International Patent Application No. PCT/EP2015/069332, dated Dec. 2, 2015.

Carter, E. A. et al., "Biological Applications of Raman Spectroscopy," Infrared and Raman Spectroscopy of Biological Materials, Jan. 2001, XP009017935, pp. 421-475.

Chrit, L., et al., "In vivo chemical investigation of human skin using a confocal Raman fiber optic microprobe," Journal of Biomedical Optics, SPIE—International Society for Optical Engineering, vol. 10, No. 4, Jul. 2005, XP002471926, pp. 44007-1-44007-11.

Examination Report as issued in Australian Patent Application No. 2015311114, dated Jun. 26, 2019.

Shao, J., et al., "In Vivo Blood Glucose Quantification Using Raman Spectroscopy" Oct. 2012, PLOS ONE 7(10): e48127, 7 pages.

* cited by examiner

METHOD AND APPARATUS FOR TRANSDERMAL IN VIVO MEASUREMENT BY RAMAN SPECTROSCOPY

CROSS-REFERENCE TO RELATED APPLICATIONS

This application is the U.S. National Stage of PCT/EP2015/069332, filed Aug. 24, 2015, which in turn claims priority to Great Britain patent application number 1415671.5, filed Sep. 4, 2014. The content of these applications are incorporated herein by reference in their entireties.

The invention relates to methods for transdermal in vivo measurement by Raman spectroscopy of glucose or other Raman detectable species present in skin. The detected component may be present in interstitial fluid.

BACKGROUND

Spectroscopy is a method for obtaining information on a molecular scale by the use of light. This information can be related to the rotational, vibrational and/or electronic states of the molecules probed as well as dissociation energy and more. The rotational and/or vibrational spectrum of a given molecule is specific for that molecule. As a consequence, molecular spectra in particular rotation and/or vibrational spectra are often referred to as 'fingerprints' related to a specific molecule. Information related to rotational, vibrational and/or electronic states of molecules can therefore be used to analyze a sample comprising a number of unknown molecular components, thereby obtaining knowledge about the molecular components in the sample.

The basis for a spectroscopic setup is a light source, e.g. a laser, which is used for illuminating a sample. The light from the light source (the incoming light) will interact with the sample, and often result in an alternation of the light which is transmitted through, emitted by, reflected by and/or scattered by the sample. By collecting the altered light and analyzing its spectral distribution, information about the interaction between the incoming light and the molecular sample can be obtained; hence information about the molecular components can be obtained.

The spectral distribution is typically measured by using a spectrophotometer. A spectrophotometer is an optical apparatus that works by separating the light beam directed into the optical apparatus into different frequency components and subsequently measuring the intensity of these components by using e.g. a CCD detector, a CCD array, photodiode or such.

The altered light reflecting interactions between the incoming light and the molecular sample can roughly be characterized as either emission or scattering if the light is collected in generally the reverse path from that on which it entered the sample. The emission signals have relatively broad spectral profiles as compared to scattering light signals, which normally display quite narrow spectral lines. One process often dominates over the other, but both processes can and most often will occur simultaneously. The intensity of the emitted light vs. the intensity of the scattered light depends among other things on the frequency and the power of the incoming light, the intensity of the incoming light at the measuring point in the sample, and the molecular components in the sample.

Scattering of light can be classified as being either elastic or inelastic and these are characterized by being spectroscopically very narrow signals. Elastic scattering is referred to as Rayleigh scattering, in which there is no frequency shift. Rayleigh scattering thus has the same frequency as that of the incoming light.

The most commonly known example of inelastic scattering is Raman scattering, in which there is an energy interchange between the molecule and the photons of the incoming light. The frequencies, i.e. the spectral distribution of the Raman scattered light will be different from that of the incoming light and uniquely reflect the specific vibrational levels of the molecule; hence it is a fingerprint spectrum. This can be used for identification of the molecular composition of the substance probed and/or the concentration of the specific molecules in the substance.

Raman scattering is a relatively weak process compared to e.g. Rayleigh scattering and fluorescence. Reduction of contributions from these other processes is thus desirable when collecting Raman scattered light. In addition, the intensity of the Raman scattered light depends strongly on the frequency and the intensity of the incoming light. If these are variable, it may therefore be essential to monitor power fluctuations in the incoming light if one is to receive reliable information about the distribution of molecular components in different samples and/or sample spots based on analysis of the collected Raman scattered light, depending on the precision needed. The same is true if the analysis of the molecular components in a sample and/or different sample spots is based on emission spectra.

Skin comprises a number of layers having different characteristics and containing different kinds of cells and structures. Various proposals for using Raman spectroscopy to measure glucose or other components in skin have been made, but none of these has to date provided a system which ensures that in any given individual collected light signals originate from below the stratum corneum by a margin that provides for a good measurement.

The skin surface is formed by the stratum corneum which consists mainly of cornified, dead, flattened skin cells and varies in thickness between individuals and between areas of the body. The concentration of components such as glucose in the interior of the stratum corneum is not in equilibrium with the interstitial fluid below the stratum corneum.

Often, it is desired to make transdermal measurements on the fingertip because of the ease with which the fingertip can be placed into the light path of a suitable instrument. However, individual variations in the thickness of the stratum corneum are relatively large in this area. Thus, the stratum corneum generally has a thickness of from 10-15 µm on most areas of the body but may be more than 10 times thicker on the palms and the soles. Finger print patterns also provide variation in the thickness of the stratum corneum over the surface of the fingertips.

WO2011/083111 describes a Raman spectrometer based apparatus for transdermal measurement of glucose which is set to derive Raman signals from a depth of 60 to 400 µm below the skin surface, typically by focusing the incoming light to a depth within the range of 200-300 µm. This is found to be broadly satisfactory, but fails with occasional subjects whose stratum corneum at the measurement site is too great.

Caspers et al; Biophysical Journal, Vol 85, July 2003, describes an in vivo confocal Raman spectroscopy method and apparatus which is said to be useful for measuring glucose. It contains however no instruction as to the depth from which the Raman scattering should be collected in a glucose measurement and there is a strong suggestion deducible from the teaching that the apparatus had not actually been tried for this purpose.

WO2008/052221 describes a method and apparatus for coherent Raman spectroscopy that transmits light through a sample surface such as skin and tissue to a focal plane within the sample to measure for instance glucose. However, no teaching is present of the importance of selecting a particular depth for the focal plane or where this should be. Indeed, it is specifically acknowledged that using the described apparatus variations in the detected signal occur when the analyte concentration is constant due to effects of skin temperature and hydration. No suggestion is present that such effects can be avoided by a careful selection of the depth from which the measurements are taken.

WO97/36540 describes determination of the concentration of e.g. glucose using Raman spectroscopy and an artificial neural network discriminator. However, the Raman signals are not selectively obtained from a particular depth and the need to compensate for non-linearities arising from signals penetrating to a depth of >500 µm is discussed.

WO00/02479 discloses a method and apparatus for non-invasive glucose measurement by confocal Raman spectroscopy of the aqueous humor of the anterior chamber of the eye. Naturally, there is no teaching of a depth at which to make optimal measurements in skin.

WO2009/149266 refers back to Ermakov I V, Ermakova M R, McClane R W, Gellermann W. Opt Lett. 2001 Aug. 1; 26(15):1179-81, 'Resonance Raman detection of carotenoid antioxidants in living human tissues.' which describes using resonance Raman scattering as a novel non-invasive optical technology to measure carotenoid antioxidants in living human tissues of healthy volunteers. By use of blue-green laser excitation, clearly distinguishable carotenoid Raman spectra superimposed on a fluorescence background are said to be obtained.

Chaiken et al (Noninvasive blood analysis by tissue modulated NIR Raman spectroscopy, J. Chaiken et. al., Proc. of SPIE optical Eng., 2001, vol. 4368, p. 134-145) obtained a correlation of only 0.63 between Raman based measurements and finger stick blood glucose measurements across several individuals, but were able to obtain a correlation of 0.90 for a single individual. The setup utilized by Chaiken et al comprises a collimated excitation beam and so naturally they do not disclose any optimal focal depth.

The present invention now provides a method for determining whether the origin of Raman signals received in transdermally operating confocal detector apparatus lies within the stratum corneum or below it, which method comprises analysing said signals to compare the relative intensities of Raman signals originating from a first skin component and Raman signals originating from a second skin component, wherein said relative intensities are indicative of whether the Raman signals originate within the stratum corneum or below the stratum corneum.

Alternatively expressed, the invention provides a method for predicting whether a spectrum of Raman signals received transdermally in a confocal detector apparatus and having at least one component expected to have an intensity representing the concentration of a skin component at a point of origin of said Raman signals below the surface of the skin will accurately represent said concentration, which method comprises analysing features of said spectrum relating to skin components other than the skin component the concentration of which is to be measured and thereby determining whether the Raman signals originate primarily within the stratum corneum so that the spectrum will be less likely to represent said concentration accurately or originate primarily below the stratum corneum so that the spectrum will be more likely to represent said concentration accurately.

The preferred features described below apply to either of these aspects of the invention.

Preferably, the method comprises analysing said signals to compare the relative intensities of Raman signals originating from a first skin component and Raman signals originating from a second skin component, wherein said relative intensities are indicative of whether the Raman signals originate primarily within the stratum corneum or primarily below the stratum corneum.

Preferably, said first skin component produces a peak in the Raman spectrum at a wavenumber of 883-884 $cm^{-1}$. This may derive from proteins, including Type I collagen (see Raman Spectroscopy of Biological Tissues, Movasaghi et al, Applied Spectroscopy Reviews 42: 493-541, 2007).

Preferably said second skin component produces a peak in the Raman spectrum at 893-896 $cm^{-1}$. This may derive from deoxyribose phosphodiester. Thus, the second skin component may be DNA.

The methods of the invention may further comprise the step of comparing the sizes of said first and second peaks and producing an output indicative that the signals arise from within the stratum corneum if the size of said first peak divided by the size of said second peak is less than a selected value R. The value of R may be chosen according to the selectivity of the determination of origin of the analyte signal that one wishes to achieve. It will generally be convenient to use the peak height as a measure of peak size but one may adopt another size measure such as area.

If R is made larger, more candidate measurements are likely to be rejected, leading to an increased need to repeat such measurements at a different measurement site, or to adjust the focussing distance of the apparatus used, or to reject the patient from this form of measurement entirely.

If R is chosen to be smaller, fewer measurements will be ruled unreliable, but the chances of a measurement being accepted that does not in reality correlate well to actual analyte concentration may be increased.

Preferably, R is selected to be at least 0.75, more preferably at least 0.95, and optionally R is set at 1.0 or higher, e.g. up to 1.25

Supposing that R is set to be 1.0, if the said 883-884 $cm^{-1}$ peak is higher than the 893-896 $cm^{-1}$ peak, this is a good indicator that the signals arise from sufficiently below the stratum corneum for the measurements of an analyte skin component in interstitial fluid to be accurate. If on the other hand the height order is reversed and the 893-896 $cm^{-1}$ peak is higher than the 883-884 $cm^{-1}$ peak, this is an indicator that the signals may not arise from sufficiently below the stratum corneum for the measurements of an analyte skin component in interstitial fluid to be accurate. However, it is expected that the value of 1.0 builds in a safety margin and R could be set lower.

Accordingly, the method may include the steps of comparing the sizes of said first and second peaks and producing an output indicative that the signals arise from within the stratum corneum if said first peak is of lesser size than said second peak and/or producing an output indicative that the signals arise from below the stratum corneum if said second peak is of lesser size than said first peak.

Other peaks in the Raman spectrum may be chosen that provide a similar indication of the depth of origin of the signals.

The above methods provide a first line test, but even if the said size relationship of the 883-884 $cm^{-1}$ peak and the 893-896 $cm^{-1}$ peak is satisfactory, this may not in all cases provide sufficient assurance and a second line check may be desirable. To this end, one may investigate whether the size of a Raman peak deriving from a third and/or the size of a Raman peak deriving from a fourth skin component, or further skin components, is greater than a predetermined size. Again, height may be adopted as a convenient measure of size.

The predetermined size for this purpose for each Raman peak used may be x standard deviations above the mean size for the respective peak as measured using the same apparatus on multiple different measurement sites on the skin of a test population of one or preferably multiple test subjects. Suitably, x may be from 0.5 to 2, e.g. 0.75 to 1.5, but is preferably 1.

Thus for instance, if the comparison of the relative intensities of Raman signals originating from a first skin component and Raman signals originating from a second skin component is indicative that the Raman signals originate primarily below the stratum corneum, the methods of the invention may further comprise determining whether the size of a further peak in the spectrum associated with a skin component which may be prevalent in the stratum corneum is more than one standard deviation greater than a mean value for the size of that peak in a statistically valid sample of similar spectra, a positive determination indicating a probability that the Raman signals do not after all originate primarily below the stratum corneum.

To obtain the similar spectra, multiple measurement sites are suitably chosen to be sufficiently numerous to provide a statistically valid measurement of the standard deviation. Suitably, 100-300 test sites, preferably chosen on from 5-20 test subjects, for instance 10 sites on each of 20 individuals could be used. The test subjects should preferably be matched for ethnicity, age, and/or nature of occupation (such as manual worker or not) with each other and the subject of the analyte measurements.

Suitable peaks for use in this second line check would be peaks at 1445 $cm^{-1}$ and at 1650 $cm^{-1}$. The former may arise from various bending modes associated with $CH_2$ and $CH_3$ groups in collagen. The latter may derive from protein amide groups.

If the first line test is failed or if either of these chosen peaks is larger than the chosen cut off size, the validity of the analyte measurement is doubtful and an alternative measurement site should be chosen or the depth from which the Raman signals originate should be suitably altered, which will generally imply that it should be increased.

The method of the invention can be used to determine whether the transdermally operating confocal detector apparatus will successfully measure the concentration of a target skin component by measuring Raman signals originating below the stratum corneum. This determination may be used simply to exclude patients from measurement who are unsuitable, or to guide a choice of a different measurement site where the stratum corneum is not too thick, or to guide an adjustment of the transdermally operating confocal detector apparatus in order to cause it to measure Raman signals originating from below the stratum corneum.

Methods according to either aspect of the invention may therefore further include adjusting said transdermally operating confocal detector apparatus in response to a finding that the Raman signals originate from within the stratum corneum, said adjustment altering the depth of origin of said Raman signals such that a new depth is determined to be satisfactory and in particular such that the depth is no longer determined to be within the stratum corneum.

This may be done by adjustment of a distance from the surface of the skin of an objective lens from which light is emitted to the measurement site and received from the measurement site, so as to alter the depth from which Raman signals are received.

Alternatively or additionally, said transdermally operating confocal detector apparatus may comprise an objective lens having a focal length and said method of altering the depth of origin of the Raman signals may comprise altering the focal length of the objective lens by replacement of the objective lens or by adjustment of the objective lens.

To this end, said transdermally operating confocal detector apparatus may comprise a compound objective lens comprising at least a first element and a second element spaced from the first element, and said method of altering the depth of origin of the Raman signals may comprise altering the spacing of two or more elements to adjust the focal length of the compound objective lens, and this would include replacement of the lens with one in which the said spacing is different.

Optionally, said adjustments of the lens position or focal length may be carried out by altering the thickness of a piezoelectric spacer, either between the objective lens and the skin surface or between said lens elements by the alteration of a voltage applied thereto.

Optionally, said adjustments of the lens position or focal length may be carried out by altering the rotational position of an annular screw mounted collar carrying at least one element of said compound lens.

The invention also provides in a further aspect transdermally operating confocal detector apparatus for non-invasive in vivo measurement by Raman spectroscopy of the concentration of a skin component present in the skin of a subject, comprising a light source, optical components defining a light path from said light source to a measurement location, a spectrum analysis unit, optical components defining a return path for Raman scattered light from said measurement location to said spectrum analysis unit, wherein said spectrum analysis unit operates to determine whether the origin of Raman signals received therein lies within the stratum corneum or below it, by analysing features of Raman scattered light relating to skin components other than the skin component the concentration of which is to be measured and thereby determining whether the Raman signals originate primarily within the stratum corneum or primarily below the stratum corneum.

Alternatively expressed, in this aspect the invention provides in a further aspect transdermally operating confocal detector apparatus for non-invasive in vivo measurement by Raman spectroscopy of the concentration of a skin component present in the skin of a subject, comprising a light source, optical components defining a light path from said light source to a measurement location, a spectrum analysis unit, optical components defining a return path for Raman scattered light from said measurement location to said spectrum analysis unit, wherein said spectrum analysis unit operates to determine whether the origin of Raman signals received therein lies within the stratum corneum or below it, by analysing said signals to compare the relative intensities of Raman signals originating from a first skin component and Raman signals originating from a second skin component, wherein said relative intensities are indicative of whether the Raman signals originate within the stratum corneum or below the stratum corneum.

Preferably, said spectrum analysis unit determines the size of a peak in the Raman spectrum at 883-884 $cm^{-1}$ produced by said first skin component.

Preferably, said spectrum analysis unit determines the size of a peak in the Raman spectrum at 893-896 cm$^{-1}$ produced by said second skin component.

Said spectrum analysis unit may determine a ratio between the size of a first peak in the Raman spectrum at 883-884 cm$^{-1}$ and the size of a second peak in the Raman spectrum at 893-896 cm$^{-1}$. Height may be used as a suitable measure of peak size.

Preferably therefore, said spectrum analysis unit produces an output indicative that the signals arise from within the stratum corneum if the height of said first peak divided by the height of said second peak is less than a selected value R. R may be pre-set to be 0.75, more preferably 0.95 and still more preferably 1.0.

Preferably, R is not more than 1.25.

Optionally, if the signal analysis unit determines that comparison of the relative intensities of Raman signals originating from a first skin component and Raman signals originating from a second skin component is indicative that the Raman signals originate primarily below the stratum corneum, said signal analysis unit further determines whether the size of a further peak in the spectrum associated with a skin component prevalent in the stratum corneum is more than x standard deviations greater than a mean value for the size of that peak in a statistically valid sample of similar spectra, a positive determination indicating a probability that the Raman signals do not after all originate primarily below the stratum corneum. The value of x is discussed above.

Said transdermally operating confocal detector apparatus may comprise a set of interchangeable objective lenses of differing focal length or an objective lens having an adjustable focal length. To this end, said objective lens may be a compound objective lens comprising at least a first element and a second element spaced from the first element, and said lens is then adjustable by altering the spacing of two or more elements to adjust the focal length of the compound objective lens. The spacing adjustment may preferably be piezoelectric or screw operated as described above. Interchangeable lenses may differ from one another in spacings of such lens elements.

The apparatus may include means for computing a concentration of glucose or another analyte component in interstitial fluid or blood based on analysis of said Raman scattered light. The Raman spectrum may be analysed by application thereto of a trained statistical model which relates peak intensities to glucose or other analyte concentration. This may be performed using partial least squares regression (PLS) as described in more detail in the references acknowledged in M. A. Arnold; In Vivo Near-Infrared Spectroscopy of Rat Skin Tissue with Varying Blood Glucose Levels; Anal. Chem. 2006, 78, 215-223 therein and in A. M. K. Enejder et al; Raman Spectroscopy for Non-invasive Glucose Measurements; Jnl of Biomedical Optics, 10(3), 031114; May/June 2005. Other forms of multivariate calibration may be used including Principal Component Analysis (PCA) in a manner analogous to that described in for instance A. G. Ryder, G. M. Connor and T. J. Glynn; Quantitative Analysis of Cocaine in Solid Mixtures using Raman Spectroscopy and Chemometric Methods; Journal of Raman Spectroscopy, 31; 221-227 (2000) or in J. T. Olesberg, L. Liu, V. V. Zee, and M. A. Arnold; In Vivo Near-Infrared Spectroscopy of Rat Skin Tissue with Varying Blood Glucose Levels; Anal. Chem. 2006, 78, 215-223. In general, statistical methods of spectrum analysis useful in calibrating detection of analytes from absorption spectra will be useful in analysis of Raman spectra also.

The apparatus may be adjustable to alter the depth below the skin surface from which most of the intensity of the Raman signals originates, so as to set said depth to be below the stratum corneum. Light collection will be from a range of depths and the apparatus may be adjustable such that a desired percentage of the light originates from, below the stratum corneum.

Preferably, said percentage is at least 55%, more preferably at least 70%, more preferably at least 90%. Preferably also, at least 90% of Raman scattered light received at the light detection unit originates at depths less than 600 μm below the skin surface. Preferably also less than 25%, more preferably less than 10%, of Raman scattered light received at the spectrum analysis unit originates at depths less than 100 μm below the surface of the skin.

Preferably, at least 40%, more preferably at least 50% of the light reaching the spectrum analysis unit originates from 200 to 400 μm below the surface of the skin.

Optionally, said adjustment is automated. Thus, the spectrum analysis unit may operate to determine the origin of the Raman signals as described and in the event of a determination that the signals originate from within the stratum corneum may output a control signal to an adjustment means which operates to adjust a confocal depth position from which Raman signals are received until the spectrum analysis unit determines the origin of the signals to be below the stratum corneum. Such adjustment means may produce a said control signal in the form of a voltage applied to a piezoelectric actuator for changing the position of at least one lens element relative to the skin in use. Alternatively, the control signal may drive a motor to rotate a rotatable lens adjustment mechanism to alter lens component spacing.

Thus the adjustment means may hunt for a satisfactory confocal depth by making iterative increases in the confocal depth until a satisfactory result is obtained. Suitably, this might entail making progressive increases in confocal depth of from 10 to 50 μm, e.g. from 20 to 30 μm.

The spectrum analysis unit may receive light from the surface of the skin without transmission of said light through an optical fibre or with such a fibre. In the latter eventuality, apparatus according to the invention may comprise a hand piece for application to the skin containing components defining said measurement location in use, and one or more optical fibres connecting said hand piece to said light source and to the spectrum analysis unit for analysis of signals received from said light detection unit to provide said measurement therefrom.

The position distal of a skin engaging member of said measurement location is optionally adjustable and can for instance be adjustable to be from 60 to 400 μm beyond said distal surface of the skin engaging member or can be adjusted to be from 50 to 400 μm, more preferably 200 to 300 μm, beneath the surface of the skin. Alternatively, however the position distal of the skin engaging member of said measurement location is fixed, suitably such that the numerical parameters discussed above are achieved.

Thus, the depth of focus of the optical components defining said light path, and/or the optical components defining said return path may be fixed rather than adjustable. It follows that in this case, if the spectrum analysis unit determines that the confocal depth is not satisfactory, an alternative measurement site should be chosen or that patient should be excluded.

The invention includes a method for non-invasive in vivo measurement by Raman spectroscopy of a component, which may be glucose, present in interstitial fluid in the skin of a subject, comprising, in either order, (a) directing light from a light source into the skin of said subject via optical components defining a light path from said light source to a measurement location in the skin and so producing Raman signals returning from the skin, determining whether the origin of the returning Raman signals lies within the stratum corneum or below it by analysing said signals to compare the relative intensities of Raman signals originating from a first skin component and Raman signals originating from a second skin component, wherein said relative intensities are indicative of whether the Raman signals originate within the stratum corneum or below the stratum corneum, and (b) directing light from said light source into the skin of said subject via said optical components defining a light path from said light source to said measurement location in the skin, receiving Raman scattered light back from the skin at a light detection unit via optical components defining a return path for Raman scattered light from said measurement location to said light detection unit, and determining said concentration from said Raman scattered light. Preferred features of step (a) above may be as previously described.

The method may further include adjusting said optical components so that the Raman signals are determined to originate from below the stratum corneum.

Such methods are preferably performed using apparatus in accordance with the invention.

The method may include calibrating the output of the apparatus by the use of the apparatus to provide an output in respect of a known concentration of the skin component to be measured prior to said measurement on said subject. Once calibrated the apparatus preferably is not calibrated again for a period of not less than a week, more preferably a month. Preferably, said calibration step of providing an output in respect of a known substance concentration is not carried out by the use of the apparatus on said subject.

Thus, the calibration may be conducted on a different subject for whom a concentration of the component is known or may be conducted using a standard reference material such as a drop of component solution placed in the measurement location or a solid phantom simulating a component solution.

Any apparatus described herein may be used in such a method.

The light source is preferably a laser. A preferred form of laser to use as the light source is a diode laser with a wavelength in the range of 300-1500 nm. Suitable preferred wavelengths are 785, 830, or 850 nm. A suitable power range is 50-1000 mW. For example, one may use an 830 nm, 500 mW FC-830 laser from RGB Lase.

The apparatus may include an optical probe for measuring light signals in which the optical components defining the light path from the light source to the measurement location comprise a first optical fibre guiding incoming light from said light source and a lens focusing said incoming light towards, i.e. into or onto, the measurement location. The optical components for defining a return path for Raman scattered light may comprise said lens and further optical components guiding the altered light to the spectral analysis unit. The further optical components may include a second optical fibre, however, instead of employing a second optical fibre, a spectrophotometer may be integrated directly into the handpiece. Optionally, there may be a further light detection unit (or light logging device) measuring intensity fluctuations in said incoming light, and this further light detection unit may advantageously be positioned after said first optical fibre, whereby said further light detection unit receives a part of said incoming light from said first fibre.

An electrical output from this light logging device which is representative of the intensity of the incoming light may be used to adjust intensity measurements in the spectrum analysis unit to compensate for variations in said intensity.

The use of at least one optical fibre is advantageous in that although a microscope can be used, a microscope-based optical probe is not a readily movable object and a user's body part could be awkward to place in a position where measurements could be made. A possibility would be for the patient to insert his/her finger or arm directly under or above the microscope objective in the microscope. Unfortunately, this is cumbersome if not impossible with most microscopes.

An optical probe employing not the whole microscope but only microscope objective(s) mounted separately on e.g. a table allows for better accessibility between probe and sample. Measurements of blood sugar levels or other skin components in a patient in vivo become more convenient as the patients arm or finger can be placed in front of the microscope objective(s) without much difficulty. However, if the chosen sample is a leg, it might prove more difficult to place it appropriately in front of the microscope objective(s).

Inside the optical probe, said light logging device will normally be positioned after a dichroic mirror, which allows a minor part of the incoming light to either pass through the dichroic mirror and onto said light logging device or to be reflected by the dichroic mirror onto said light logging device. Alternatively, a splitting device can be positioned between said first fibre and said dichroic mirror, where said splitting device reflects a minor part of the incoming light onto said light logging device.

One advantage with using a light logging device is that it allows for a precise measure of the variations in the intensity of the incoming light at all material times. This ensures that variations in the intensity of the altered light due to variations in the incoming light and not sample variations can be compensated for.

In an embodiment of the invention, said lens focusing incoming light towards said sample is arranged at the surface of said optical probe such that said lens is in direct contact with the skin during measuring.

An advantage with having the lens in direct contact with the skin during measurement is that the sample penetration depth, and thereby the distance from the optical probe to the sample focus point, is known exactly, as it is defined by the focal length of the lens.

In another embodiment of the invention, said optical probe further comprises a window, where said window is positioned between said lens and the skin, such that said window is in direct contact with the skin during measuring, and where the thickness of said window is smaller than the focal length of said lens.

An advantage with inserting a window between the lens and the skin is that it can provide an easier cleaning of the optical probe, if a fragile lens sensitive to cleaning is used.

Another advantage with inserting a window between the lens and the skin is that the penetration depth can be varied depending on the thickness of the window. This provides one way of setting the penetration depth to a value resulting in a determination that the Raman signals measured originate below the stratum corneum.

Equally, instead of having a solid window, a window aperture can be provided between the lens and the skin, the aperture being formed in a skin engaging member.

The optical probe according to the invention, may further comprise a dichroic mirror positioned after said first optical fiber, where said dichroic mirror reflects any percent between re_in=0 and 100 (e.g. 90%) and transmits any percent between tr_in=0 and 100 (e.g. 10%) of said incoming light, where re_in+tr_in=100 percent (ignoring losses), and reflects any percent between re_se=0 and 100 (e.g. 30%) and transmits any percent between tr_se=0 and 100 (e.g. 70%) of said altered light, where re_se+tr_se=100 percent (ignoring losses). Hence said dichroic mirror may reflect most of the incoming light and transmit most of the altered light.

Said dichroic mirror is normally positioned at an angle of 45 degrees in relation to the propagating direction of said incoming light out of said first optical fibre.

In an embodiment where most of the incoming light is reflected by the dichroic mirror, said light logging device may be positioned after said dichroic mirror, whereby said light logging device measures intensity fluctuations in said incoming light transmitted through said dichroic mirror.

In another embodiment where most of the incoming light is reflected by the dichroic mirror, a splitting device may be positioned between said first optical fibre and said dichroic mirror, whereby said light logging device measures intensity fluctuations in said incoming light reflected of by said splitting device.

In an embodiment of the invention, said dichroic mirror is transmitting most (e.g. ≥90%) of the incoming light whilst passing a minor portion (e.g. ≤10%) and is reflecting most of the altered light (e.g. ≥70%) whilst passing a smaller amount (e.g. ≤30%).

In an embodiment where most of the incoming light is transmitted by the dichroic mirror, said light logging device may be positioned after said dichroic mirror, whereby said light logging device measures intensity fluctuations in said incoming light reflected by said dichroic mirror.

An advantage of having the light logging device situated directly after said dichroic mirror is that it utilizes the part of the incoming light, which is not reflected by the dichroic mirror, and otherwise would be lost. There is consequently no need for any additional optical components to be inserted inside the optical probe in order collect light for measuring of the fluctuations in the incoming light.

In one embodiment of the invention, the angle α between the direction of light out of said first optical fibre and the direction of light entering a said second optical fibre is substantially α=90 degrees. The angle could also be in the range α=80-100 degrees.

In one embodiment of the invention, said optical probe further comprises at least a first aperture where said first aperture only allows altered light from the focus point in the skin to reach the spectrum analysis unit thereby ensuring depth confocality. Said aperture can be a separate element, but a narrow opening of a second fiber can equally well function as said aperture when a second fibre is used.

An advantage with using an optical aperture positioned before the spectrum analysis unit is that the optical aperture works as a 3D depth filter eliminating optical signals generated outside of the confocal depth, i.e. the sample focus spot. The advantage with using a confocal optical probe is that the altered light entering the spectrum analysis unit arises solely from interactions between the incoming light and the skin at the focus depth; hence contributions from the cone-like areas above and below the focus spot are minimized or eliminated.

In another embodiment of the invention, one or more apertures can additionally be employed to obtain a sharper contrast in the z (depth) direction. A second aperture is preferably positioned between the skin and the lens focusing the light into the sample. This second aperture can be a separate element, but a narrow opening of the optical probe at the point where light exits/is collected by the lens can equally well function as an aperture.

Although apparatus according to the invention is designed and configured for measuring optical signals in the skin in vivo, it could also be employed for measuring optical signals by immersing it into e.g. a blood sample thereby making the measurement in vitro.

Generally, the optical elements found inside an optical probe of apparatus according to the present invention are enclosed by a cover. A preferred optical probe can be moved around freely due to the use of a flexible fibre for guiding light into and optionally out of the optical probe. This enables easy in vivo measurements of e.g. blood sugar levels in a patient using different body areas such as an arm, a finger, a leg or similar. The apparatus may however be constructed so that the optical components are contained in a housing which defines a specific location on which to place a fingertip pad for performance of the measurement.

The stratum corneum thickness of a fingertip pad will typically be from 10-40 μm (see Marks, James G; Miller, Jeffery (2006). Lookingbill and Marks' Principles of Dermatology (4th ed.). Elsevier Inc. Page 7. ISBN 1-4160-3185-5 and Thickness of the Stratum Corneum of the Volar Fingertips H. FRUHSTORFER, U. ABEL, C.-D. GARTHE, AND A. KNU"TTEL. Accordingly, the preferred measurement depths of 200-300 μm will be from 160 to 190 μm up to 260 to 290 μm below the stratum corneum. Depths of measurement for all skin areas are preferably from 50 to 390 μm, more preferably from 190 to 290 μm below the stratum corneum.

A primary application of the apparatus is generally to measure blood sugar levels in a patient. The level of glucose in blood correlates with the level in interstitial fluid at the selected depth. Other analytes which may be measured in the same way would include lactate, haemoglobin, cholesterol, alcohol, urea and/or drug.

BRIEF DESCRIPTION OF THE DRAWINGS

The invention will be further described and illustrated by reference to the accompanying drawings in which.

DESCRIPTION OF PREFERRED EMBODIMENTS

Figure 1:
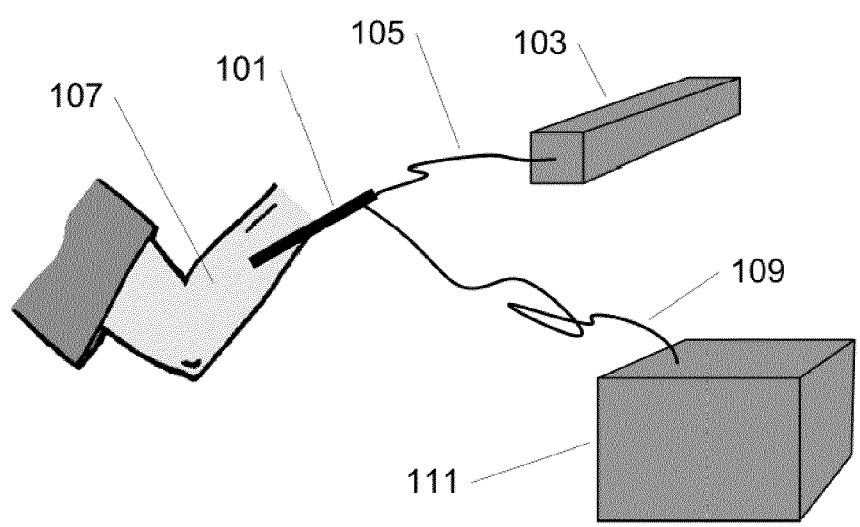
FIG. 1 shows schematically apparatus according to the invention.

FIG. 1 schematically shows apparatus according to the invention in use for measuring the concentration of glucose (or another skin substance) in vivo. An optical probe 101 receives light from a light source 103 through an incoming light fibre 105. In this embodiment of the invention, the light source 103 is a laser. The incoming light illuminates and interacts with the skin 107. Altered light received back from the skin, is collected by the optical probe 101 and is analysed in a spectrophotometer within the probe to produce an electrical output which is sent via a connection 109 to a computer 111 for subsequent analysis of the spectral components. Within the spectrophotometer there is a light detection unit. Alternatively, of course, the spectrophotometer function could be performed externally to the hand piece and light could be communicated from the handpiece to the spectral analysis unit via a second optical fibre.

In this embodiment of the invention, the optical probe is applied to a patient's arm, but it could also be applied to a finger or another body part. Likewise, the measurement is displayed as being carried out in vivo, but the optical probe 101 could also be employed for measuring optical signals by immersing it into e.g. a blood sample thereby making the measurement in vitro.

Generally, the optical elements found inside the optical probe 101 of the apparatus according to the present invention are enclosed by a cover, where the cover has at least one opening for the incoming light fibre 105 and the outgoing electrical signal connection 109 and an opening for the outgoing light employed to illuminate the sample. The latter opening can also be used for collecting the altered light from the sample. The optical probe 101 can be moved around freely due to the use of flexible a fibre for guiding light into the optical probe. This enables easy in vivo measurements of e.g. blood sugar levels in a patient using different body areas such as an arm, a finger, a leg or similar.

A primary application of the optical probe 101 is to measure blood sugar levels in a patient. The probe can however also be used for measuring e.g. the level of lactate haemoglobin, cholesterol, alcohol, urea and/or drug in the blood or the temperature and/or variations of the temperature in the blood.

Figure 2:
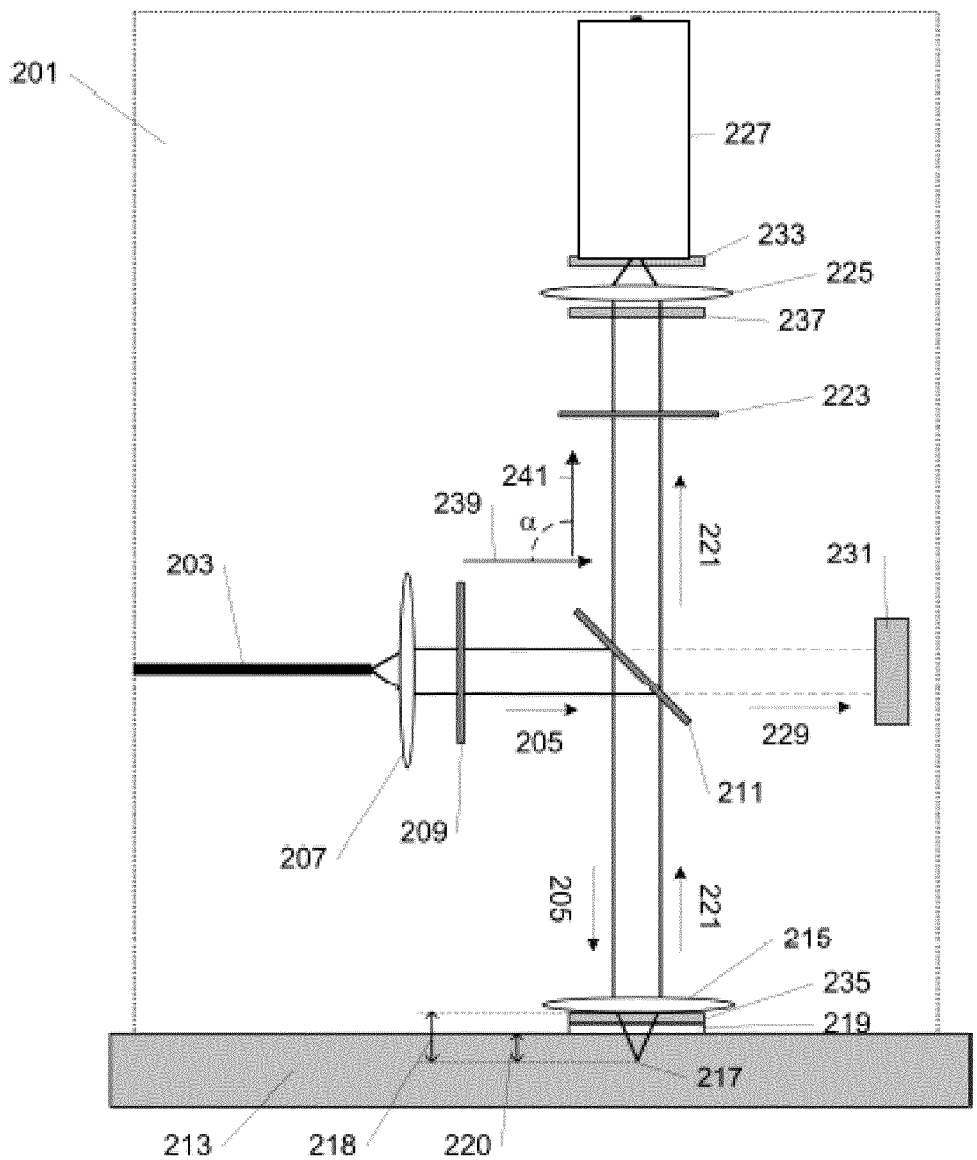
FIG. 2 shows a first embodiment of an optical probe forming part of the apparatus of FIG. 1.

FIG. 2 shows a first embodiment of the optical probe 201 comprising an incoming light optical fibre 203 for guiding light into the optical probe 201. According to this embodiment of the invention, the light source is normally a laser. Upon exiting the first fibre 203, the incoming light 205 is collimated using a first lens 207, which is an objective lens, and optically filtered by passing through a first filter 209 blocking any percentage between 0 and 100, e.g. from 75 to 100 percent, of frequencies/wavelengths outside the laser frequency/wavelength. Blocking of frequencies outside the laser frequency ensures that e.g. Raman scattering generated inside the first fibre 203 is removed from the incoming light 205. The first filter 209 may also block any percentage between 0 and 100, e.g. from 0 to 50 percent, of the laser frequency. This is an advantage if the intensity of the incoming light 205 is too high for the requirements of the sample. The first filter 209 is preferably a band-pass filter, a notch filter, an edge filter or such.

The optical probe 201 further comprises a dichroic mirror 211 that either reflects or transmits any percentage between 0 and 100 of the light, where the percentage of reflected and transmitted light is dependent on the coating on the dichroic mirror 211, the angle at which the light hits the dichroic mirror 211, and the frequency of the light. The dichroic mirror 211 can e.g. be coated such that it reflects the highest percent of the incoming light 205 when the dichroic mirror 211 is positioned at a given angle in relation to the direction of the incoming light 205. Changing the angle between the dichroic mirror 205 and the incoming light 205 will therefore reduce the percent of incoming light 205 reflected by the dichroic mirror 211.

In this embodiment of the invention, most of the incoming light 205 is reflected by the dichroic mirror 211 and focused inside the skin 213 of a subject by a second lens which is an objective lens 215. The focus point 217 of the incoming light 205 is defined by the focal length 218 of the second lens 215 and the distance distal of the lens of a skin engagement member 219 and in particular its distal surface which engages the skin in use. The skin engagement member may take the form of a window as shown. Alternatively, it may be a collar around the objective lens. Optionally, the extent to which the skin engaging surface of the collar extends beyond the objective lens itself may be adjustable, suitably by screw threads connecting the collar and the lens. This may be used to adjust the depth below the skin at which the incoming light is focussed. Alternatively, a set of objective lenses may be provided, each having a collar in which the extent to which the skin engaging surface of the collar extends beyond the objective lens itself is different, whereby a desired depth of focus may be obtained by replacement of one objective lens with another. In a further option, the skin engaging member may instead by the distal surface of the objective lens itself. The second lens 215 is preferably convex, but could also be aspheric or planar. As described in more detail hereafter particularly with reference to FIG. 5, the focal length of the lens 215 may be variable and may be controlled according to the output of the spectrum analysis unit.

The dichroic mirror 211 is in the current embodiment positioned at an angle of 45° in relation to the propagating direction of the incoming light 205. The majority of the incoming light 205 is consequently reflected at a 90° angle. The dichroic mirror 211 could be positioned at an angle between 0-90° as well.

In one embodiment of the invention, the percent of the incoming light 205 which is reflected (re_in) and transmitted (tr_in) by the dichroic mirror 211 is re_in≥90% of (re_in+tr_in) and tr_in≤10% of (re_in+tr_in).

In another embodiment of the invention, the percent of the incoming light 205 which is reflected and transmitted by the dichroic mirror 211 is re_in≥98% of (re_in+tr_in) and tr_in≤2% of (re_in+tr_in), respectively.

The illustrated optical probe 201 further comprises an optional thin window 219, which is positioned between the second lens 215 and the skin 213. The thickness of the window 219 is smaller than the focal length of the second lens 215, i.e. smaller than the distance from the second lens 215 to the focus point 217 inside the skin 213. The window 219 can serve to protect the second lens 215 thereby enabling easy cleaning of the optical probe 201 after it has been in contact with the skin 213. The window 219 acts as a skin engaging member and the distance from the skin engaging surface thereof to the focal point of the lens 215 determines the depth 220 below the surface of the skin at which Raman signals are generated. This is ideally set such that most of the laser light intensity is focused at 250 μm below the skin surface and/or at least 100 μm below the bottom of the stratum corneum, for instance from 100 μm to 150 μm below the bottom of the stratum corneum. If it is desired that the apparatus can be adapted for other uses, provision may be made for installing windows 219 of different thicknesses, thereby altering the sample penetration depth 220. Typical alternative sample penetration depths 220 are in the rage between 150 to 500 μm depending on the focal length 218 of the second lens 215 and the thickness of the window 219. Both shorter and longer penetrations depths 220 can also be obtained.

In another embodiment of the invention, there is no window, and the second lens 215 is in direct contact with the skin 213. The focal length of the lens for light passing through the skin will then ideally be 200-300 μm. Again, if it is desired that the apparatus can be adapted for other uses as well, the lens may be made replaceable with lenses of other focal lengths.

In addition to focusing the incoming light 205 into the skin 213, the second lens 215 collimates the altered light 221 from the focus point 217. In the current embodiment, the dichroic mirror 211 transmits the majority of the altered light 221, but reflects backscattering of the incoming light 205. This filters unwanted frequencies, i.e. the frequency of the back reflected incoming light 205, from the altered light 221 generated as a result of interactions with the skin 213.

In one embodiment of the invention, the percent of the altered light 221 which is reflected (re_se) and transmitted (tr_se) by the dichroic mirror 211 is re_se≤30% of (re_se+tr_se) and tr_se≥70% of (re_se+tr_se), respectively.

In another embodiment of the invention, the percent of the altered light 221 which is reflected and transmitted by the dichroic mirror 211 is re_se≤10% of (re_se+tr_se) and tr_se≥90% of (re_se+tr_se), respectively.

The altered light 221 is further optically filtered by passing through a second filter 223 before the light is focused by a third lens 225 into a spectrophotometer 227 acting as a spectrum analysis unit. The second filter 223 is preferably a band-pass filter, a notch filter, an edge filter or such and is characterized by transmitting any percentage between 30 and 100, e.g. 75 to 100%, of the altered light 221 collected by the second lens 215 and by blocking any percentage between e.g. 75 to 100%, of frequencies close to equal to the frequency of the incoming light. This can e.g. insure that the percentage of unwanted Rayleigh scattering passing through the second filter 223 is negligible at the same time as nearly all Raman light scattered from the skin 213 are allow to pass through.

A second filter 223 may be provided which further blocks directly reflected light close to the laser wavelength whilst allowing the Rayleigh scattered emission to pass through.

In this embodiment of the invention, the dichroic mirror 211 does not reflect all of the incoming laser light 205. Instead it allows a smaller fraction of the light 229 to pass through the dichroic mirror 211 and onto a light intensity measurement device/logging device 231, which detects the intensity and/or power of the light 229 after passing through the dichroic mirror 211 and provides a measurement output in the form of an electronic signal such as an output voltage. The light logging device 231 can be a photodiode, a CCD detector, a thermal transistor or a fibre guiding to such a device, or similar.

One advantage with using a light logging device 231 is that it allows for a precise measure of the variations in the intensity of the incoming light at all times. This ensures that variations in the intensity of the altered light 221 due to drift in the intensity of the laser light can be compensated for to prevent apparent analyte concentration variations that would otherwise be caused by variations in the incoming light intensity. The signal recorded by the light detection unit in the spectrophotometer is normalized using the measured value of the intensity of the primary light. The normalization may be done in software when the data is analysed and not in real time.

Incorporating the light logging device 231 into the optical probe 201 and having it positioned after coupling the incoming light 205 out of the first fibre 203 is a clear advantage, since the process of coupling laser light into a fibre is quite sensitive to both the angle at which the laser light is focused into the fibre and the distance between the focus point of the lens, which focuses the laser into the fibre, and the fibre itself. Variations in the intensity of the light exiting the fibre will thus vary as a result of the efficiency by which the laser light is coupled into the fibre. Using a light logging device positioned between the laser and the fibre will therefore not give a precise measure of the intensity variations of the light focused into the skin. However, measuring the variation in the incoming light intensity at the light source or at any point between the light source and the skin is within the invention in this and other embodiments.

In addition to the above described optical elements, the optical probe 201 may also be equipped with at least a first optical aperture 233 positioned before the spectrophotometer 227. The first optical aperture 233 works as a 3D depth filter eliminating optical signals generated outside of the confocal area, i.e. the focus point 217. The advantage with using a confocal optical probe is that the altered light 221 entering the spectrophotometer 227 arise solely from interactions between the incoming light 205 and the skin 213 at the focus point 217; hence contributions from the cone-like areas above and below the focus spot 217 are eliminated.

According to this first embodiment of the invention, the first aperture 233 is constructed as a separate element. However, a narrow opening of a second fiber (if present) connecting to the spectrophotometer 227 can equally well function as a first aperture 233.

In addition to the first aperture 233, one or more apertures can be employed to obtain a sharper contrast in the z (depth) direction. A second aperture 235 is preferably positioned between the second lens 215 and the skin 213. In a preferred embodiment, where there is no window 219 and the second lens 215 is convex or plano-convex, the second lens 215 will still be in direct contact with the skin 213 even with the thin second aperture 235 positioned between the skin 213 and the second lens 215.

In the current embodiment of the invention, the second aperture 235 is constructed as a separate element. However, a narrow opening of the optical probe 201 at the point where light exits/is collected by the second lens 215 can equally well function as a second aperture 235.

A third aperture 237 can preferably be positioned just before the third lens 225 as shown in the current figure. This can further improve the contrast in the z direction.

The fibre 203 and the spectrophotometer 227 are normally arranged such that the direction 239 of the light exiting the first fiber 203 and the direction 241 of the light entering the spectrophotometer 227 are at an angle of $\alpha=90°$ in relation to one another. Alternative arrangements of the two components and consequently the direction of the light exiting/entering them (239 and 241, respectively) can also be found, yielding an angle $\alpha \neq 90°$.

The fibre 203 and a second fibre if present are preferably multimode mode fibres, but could also be single mode fibers.

Figure 5:
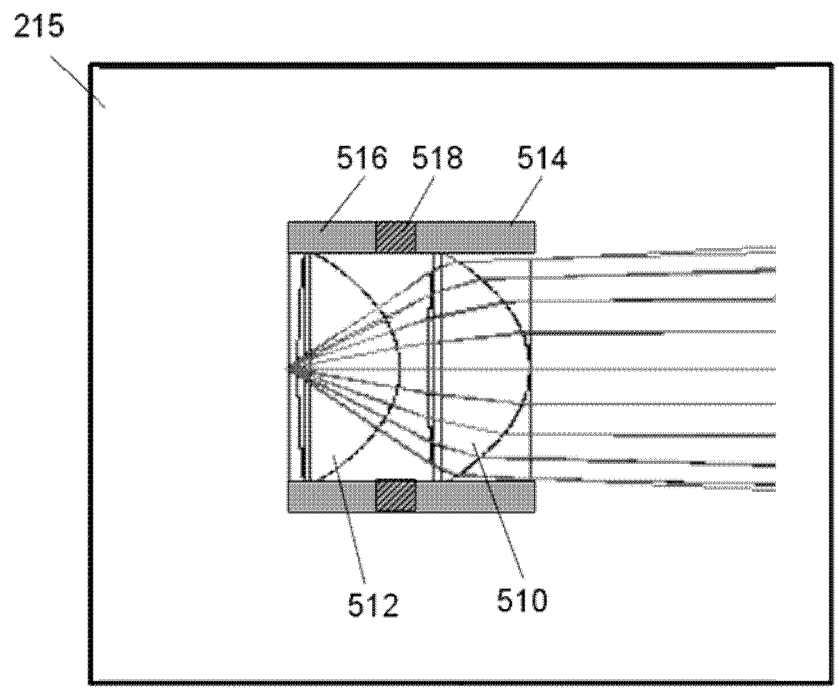
FIG. 5 shows a cross-section through a first example of an objective lens having a variable spacing between lens elements suitable for use in any of the optical probes of FIGS. 2-4.

Details of one option for the objective lens 215 are seen in FIG. 5. Here, the lens is a compound lens having first and second elements 510 and 512, element 512 being positioned distal with reference to element 510. The two lens elements are mounted in respective sections 514, 516 of a cylindrical housing between which sections is provided a piezoelectric ring element 518. Means are provided (not shown) for applying a voltage to the ring element 518 to cause its axial length to vary by displacing section 514 with respect to section 516, whereby the location of the focal point of the lens 215 is altered.

Figure 6:
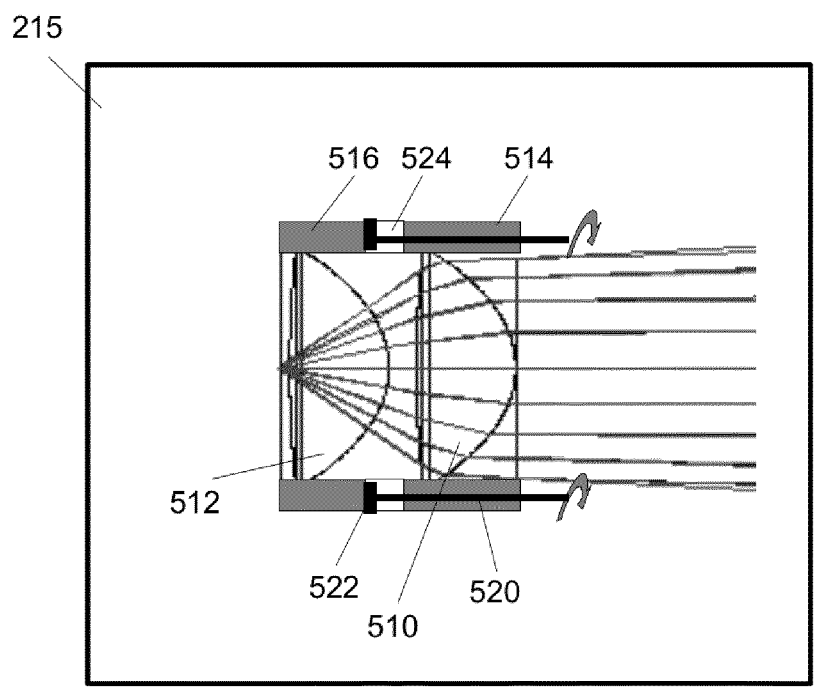
FIG. 6 shows a cross-section through a second example of an objective lens having a variable spacing between lens elements suitable for use in any of the optical probes of FIGS. 2-4.

In FIG. 6, an alternative form of variable focal length objective is shown in which the section 514 is female screw threaded and is mounted on a male screw threaded cylinder 520 fixed to the section 516 at an annular head 522. The sections 514 and 516 are spaced by a variable gap 524. The pitch of the screw thread is sufficiently fine to provide the necessary control of the focal length. Rotation of the section 514 displaces the axial position of section 514 along the cylinder 520 to alter the focal length of the objective.

A further alternative is for the objective lens to be interchangeable and for a plurality of different fixed focal length objective lenses to be provided or as mentioned above for a plurality of objective lenses of the same focal length to be provided, each having a different skin engaging member so as to define different depths of focusing.

Figure 11:
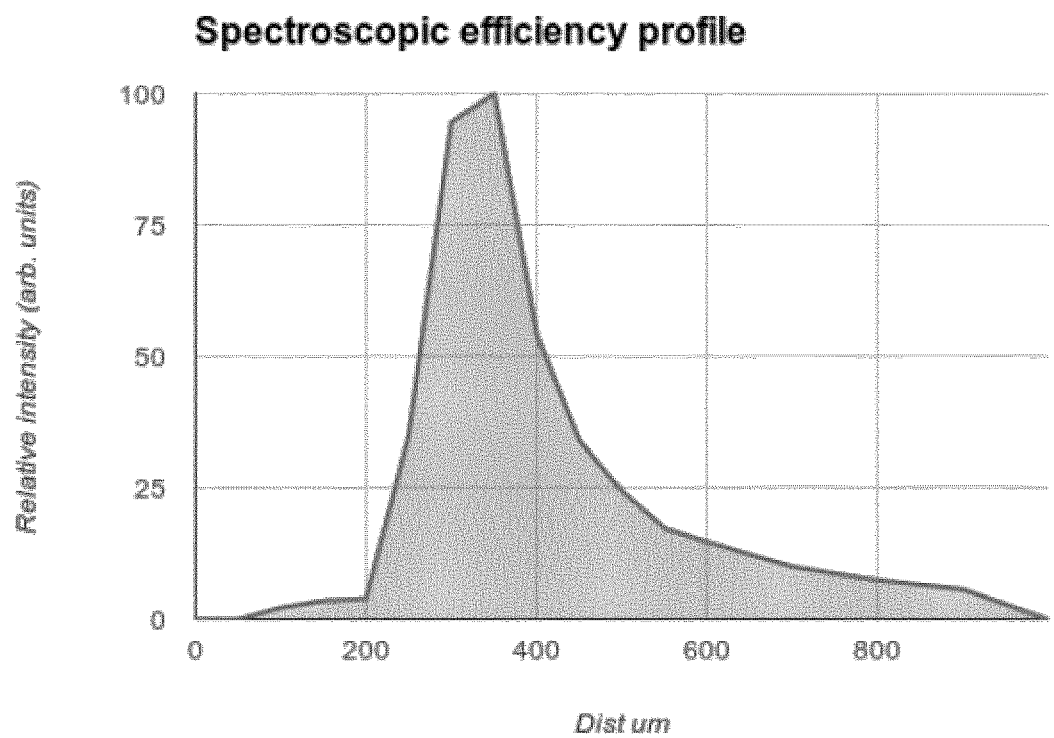
FIG. 11 shows a plot of the relative intensity of Raman signals received in suitably adjusted probes of the kind seen in FIGS. 2-4 against the depth of origin in the skin of the signals.

FIG. 11 shows the desirable depth profile for the origin of Raman signals as received in the probe and passed to the spectrophotometer. The depth origin is the surface of the skin. The relative intensity indicates the probability of a photon arising from a given depth reaching the spectrophotometer. Photons arising less than 200 μm below this have a poor chance of reaching the spectrophotometer detector. Most of the received photons originate between 250 and 400 μm below the skin surface. The intensity of Raman peaks associated with the concentration of a chosen analyte such as glucose in interstitial fluid are then likely to provide an accurate basis for measurement.

In order to verify that the measured glucose Raman signals are originating in the interstitial fluid and not in the stratum corneum, according to the invention the intensities of other peaks of the Raman spectrum are analyzed. Typical spectra are seen in FIG. 7.

It may be observed that in the majority of these spectra, the peak at 883-884 $cm^{-1}$ is somewhat higher than the peak at 893-6 $cm^{-1}$. For these spectra it has also been found that the height of peaks associated with glucose correlates well with blood glucose measurements of a chemical nature.

Figure 7:
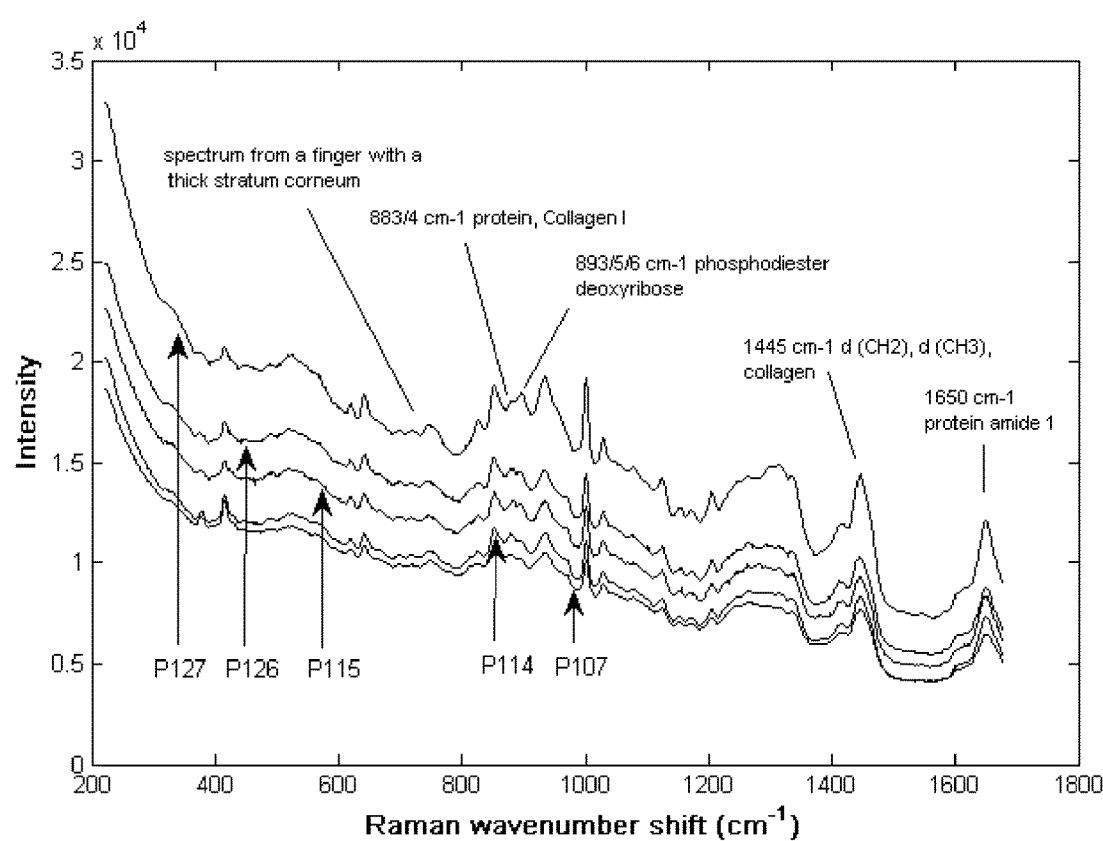
FIG. 7 shows Raman spectra obtained from several different measurement subjects identified by patient number. At the Raman wavenumber shift value of 600 cm$^{-1}$, the patient numbers relating to the spectra in descending order of the spectral curves are patient number 127, 126, 115, 114, 107.

The spectrum from patient no. 127, which is uppermost in FIG. 7, did not provide such a good correlation. The ratio of the height of the 883-884 $cm^{-1}$ peak to the height of the 893-6 $cm^{-1}$ peak in this instance was less than 0.75, being on average over several measurements only 0.34. This patient had an unusually thick stratum corneum at the measurement site. OCT measurements show that for this patient, the stratum corneum thickness measured in the finger pulp region was from 350-500 μm when for patient 114 it was from 150 to 300 μm. For patient 114, the average of the peak height ratio over several measurements was 1.23. In the spectrum for patient 127, the height order of these two peaks is reversed.

Figure 8:
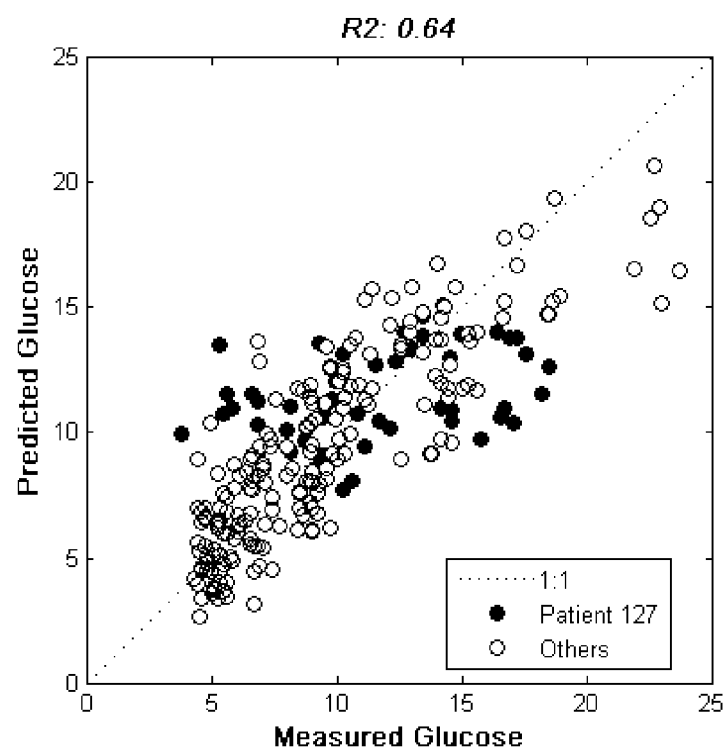
FIG. 8 shows a plot of glucose concentration predicted by the apparatus (vertical axis) against actual glucose concentrations (horizontal axis) measured by chemical analysis of blood for numerous patients. The solid points derive from patient no. 127.

FIG. 8 shows a plot of predicted glucose obtained using the invention against chemically measured glucose for numerous patients and it can be seen that the measurements obtained from patient 127 (solid points) do not share in the general good correlation between Raman and chemical measurement.

Figure 9:
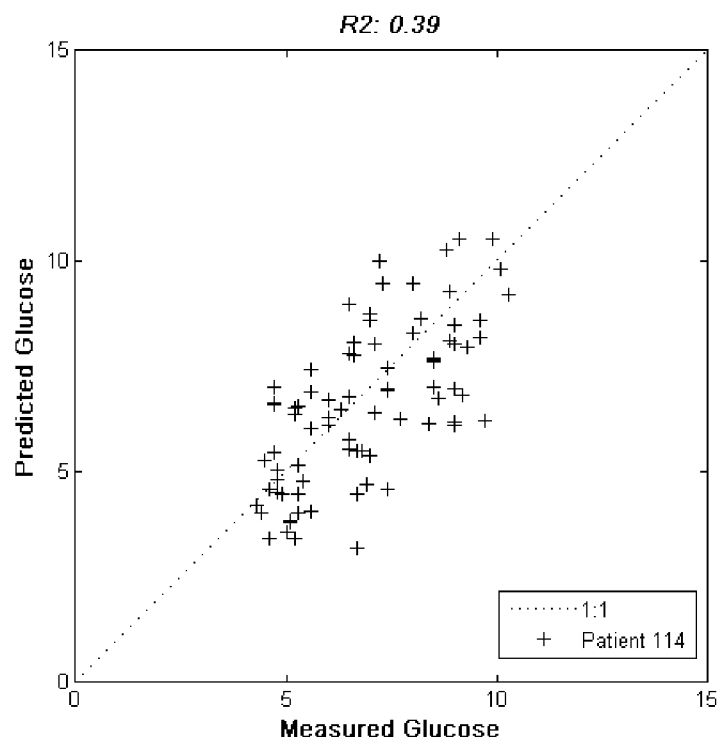
FIG. 9 shows a plot of glucose concentration predicted by the apparatus (vertical axis) against actual glucose concentrations (horizontal axis) measured by chemical analysis of blood for patient 114 in numerous repeat measurements.

FIG. 9 shows a similar correlation plot for several different measurements performed on one patient (patient 114). This may be contrasted with the solid points in FIG. 8.

As seen in FIG. 7, the spectrum for each patient has a rising background or baseline level towards shorter wavenumbers. The peak heights are measured from the local baseline level.

After location of the peak position the peak baseline can be estimated by taking the baseline level on each side of the peak. The baseline height on each side is averaged and is subtracted from the intensity in the peak maximum to generate the baseline corrected peak height. Alternatively, a windowed polynomial baseline could be estimated by an iterative approach and could be subtracted in a narrow specified region around the peak. This will move the baseline of the spectral region to around 0 and thereby remove the baseline under the peak.

In the spectrum from patient no. 127, it is also noticeable that the peaks at wavenumbers 1445 $cm^{-1}$ and 1650 $cm^{-1}$ are unusually large. Where the peak at 883-884 $cm^{-1}$ is somewhat higher than the peak at 893-6 $cm^{-1}$ but the peaks at wavenumbers 1445 $cm^{-1}$ and 1650 $cm^{-1}$ are unusually large, there may be grounds for distrusting the suitability of the measurement depth.

Figure 10:
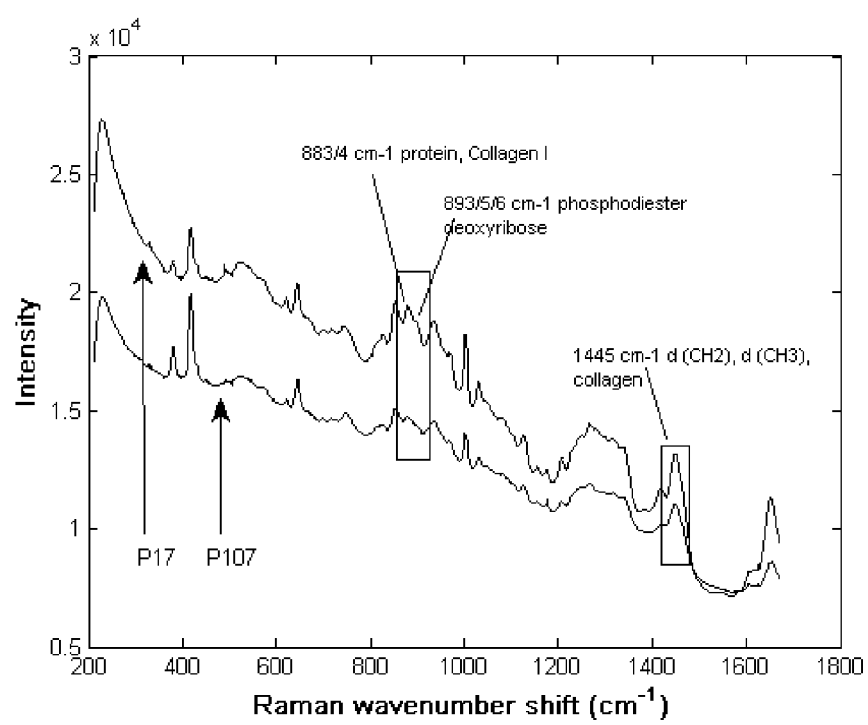
FIG. 10 shows a first patient derived Raman spectrum obtained from patient 17 (upper trace), and a second patient derived Raman spectrum obtained from patient 107 (lower trace). Both are characterised by a ratio of peak heights at 883:893 wave numbers which is greater than one, but the upper trace is characterised also by having a higher than normal peak at wavenumber 1445 cm$^{-1}$.

As seen in FIG. 10, even where the ratio of peak heights of the 883-884 $cm^{-1}$ peak and the 893-6 $cm^{-1}$ peak is greater than one, it is possible that the height of the 1445 $cm^{-1}$ and 1650 $cm^{-1}$ peaks may be unusually large. In FIG. 10, the said ratio for both the patient 17 (upper) spectrum and the patient 107 (lower) spectrum is greater than one, but the height of the 1445 $cm^{-1}$ peak for patient 17 is substantially greater than for patient 107. It was found that the Root Mean Square Error of Prediction Cross Validation (RMSEPCV) on the measurements for patient 17 was 10.7 mmol/l whereas on average it has been found to be only 2.5 mmol/l. Accordingly, it may be preferred to reject the measurement for a patient like patient 17 and to seek a better measurement site.

Either or both of these peaks may be regarded as unusually large if based on a multiplicity of measurements, they are more than one standard deviation above the mean for such measurements, as explained above.

Where either the ratio of the peaks at wavenumber 883-884 $cm^{-1}$ and 893-6 $cm^{-1}$ is below 0.75 or other selected cut off number R, or the peaks at wavenumbers 1445 $cm^{-1}$ and 1650 $cm^{-1}$ are unusually large, such that there is cause to distrust the suitability of the arrangement for measuring the concentration of an analyte skin component, one may select an alternative measurement site. Alternatively, the probe may be adjusted manually or by an automatic process so as to alter the depth from which the Raman signals originate. This would have the effect of pushing to the right the location of the peak in FIG. 11. Thus, the user may adjust the probe to increase the depth below the skin surface at which the lens is focused and may repeat the peak height analysis. Alternatively, the probe may be adjusted by input from the computer 111 to alter the focusing depth until the required peak height relationships are achieved.

These spectrum analysis and lens adjustment provisions apply to all of the following modified embodiments equally.

Figure 3:
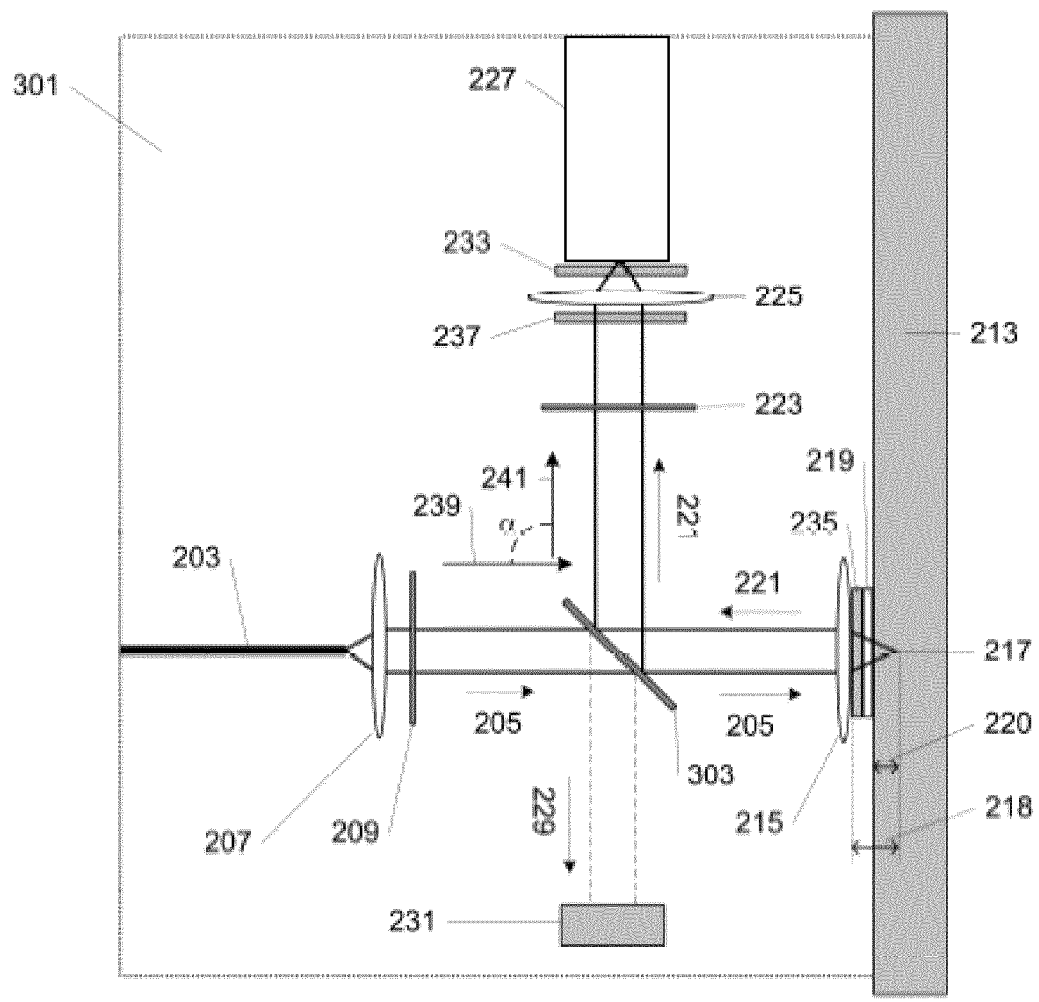
FIG. 3 shows a second embodiment of an optical probe forming part of the apparatus of FIG. 1.

FIG. 3 shows a second embodiment of the invention, where the optical probe 301 comprises an incoming light optical fibre 203 for guiding light into the optical probe 301, a first lens 207 for collimating the incoming light 205, a first filter 209 blocking any percentage between 0 and 100 of frequencies outside the frequency of the incoming light, a second lens 215 focusing the incoming light 205 into and for collecting the altered light 221 from the skin 213, a second filter 223 for optically filtering the altered light 221, a third lens 225 for focusing the altered light 221 into a spectrophotometer 227, and a light logging device 231, which detects intensity variations in the incoming light.

The fibre 203 and any second fibre that may be present are preferably multimode mode fibres, but could also be single mode fibres. The fibre 203 and the spectrophotometer 227 are normally arranged such that the direction of the light exiting the first fibre 203 and the direction of the light entering the spectrophotometer 227 are perpendicular in relation to one another. Alternative arrangements of these components 203 and 227 and consequently the direction of the light exiting/entering them can also be used.

The two filters 209 and 223 are normally a band-pass filter, a notch filter, an edge filter or such. The second lens 215 is preferably convex, but could also be aspheric or planar.

The optical probe 301 further comprises a dichroic mirror 303 that either reflects or transmits any percentage between 0 and 100 of the light. The dichroic mirror 303 is in the current embodiment positioned at an angle of 45° in relation to the propagating direction of the incoming light 205, but could also be positioned at an angle between 0-90° as well.

According to the second embodiment of the invention, the dichroic mirror 303 allows the majority of the incoming light 205 to pass through the dichroic mirror 303 and reflects only a smaller part 229 of the incoming light which is detected by the light logging device 231. The altered light 221 is reflected by the dichroic mirror 303 at an approximate 90 degree angle.

In one embodiment of the invention, the percent of the incoming light 205 which is reflected and transmitted by the dichroic mirror 303 is $re\_in \leq 30\%$ of ($re\_in+tr\_in$) and $tr\_in \geq 70\%$ of ($re\_in+tr\_in$), respectively, and the percent of the altered light 221 which is reflected and transmitted by the dichroic mirror 303 is $re\_se \geq 70\%$ of ($re\_se+tr\_se$) and $tr\_se \leq 30\%$ of ($re\_se+tr\_se$), respectively.

In another embodiment of the invention, the percent of the incoming light 205 which is reflected and transmitted by the dichroic mirror 303 is $re\_in \leq 10\%$ of ($re\_in+tr\_in$) and $tr\_in \geq 90\%$ of ($re\_in+tr\_in$), respectively, and the percent of the altered light 221 which is reflected and transmitted by the dichroic mirror 303 is $re\_se \geq 90\%$ of ($re\_se+tr\_se$) and $tr\_se \leq 10\%$ of ($re\_se+tr\_se$), respectively.

The optical probe 301 may further optionally comprises a thin window 219 constituting a skin engaging member, which is positioned between the second lens 215 and the skin 213, a first optical aperture 233, second aperture 235 normally positioned between the second lens 215 and the skin 213, and a third aperture 237 normally be positioned just before the third lens 225. According to this second embodiment of the invention, the apertures 233 and 235 are formed in separate elements. However, a narrow opening of a second fibre communicating with the spectrophotometer 227 can equally well function as a first aperture 233 and a narrow opening of the optical probe 301 at the point where light exits/is collected by the second lens 215 can equally well function as a first aperture 233.

The skin penetration depth 220 is again set ideally at 200 (or 210)-300 µm. It can in addition be made adjustable for other uses and again, typical sample penetration depths 220 are then in the rage between 150 to 500 µm depending on the focal length 218 of the second lens 215 and the thickness of the window 219, if such is part of the optical probe 301. Both shorter and longer penetrations depths 220 can also be obtained.

The advantages with the optical probe 301 are the same as the ones described in relation to the optical probe 201 shown in FIG. 2.

Figure 4:
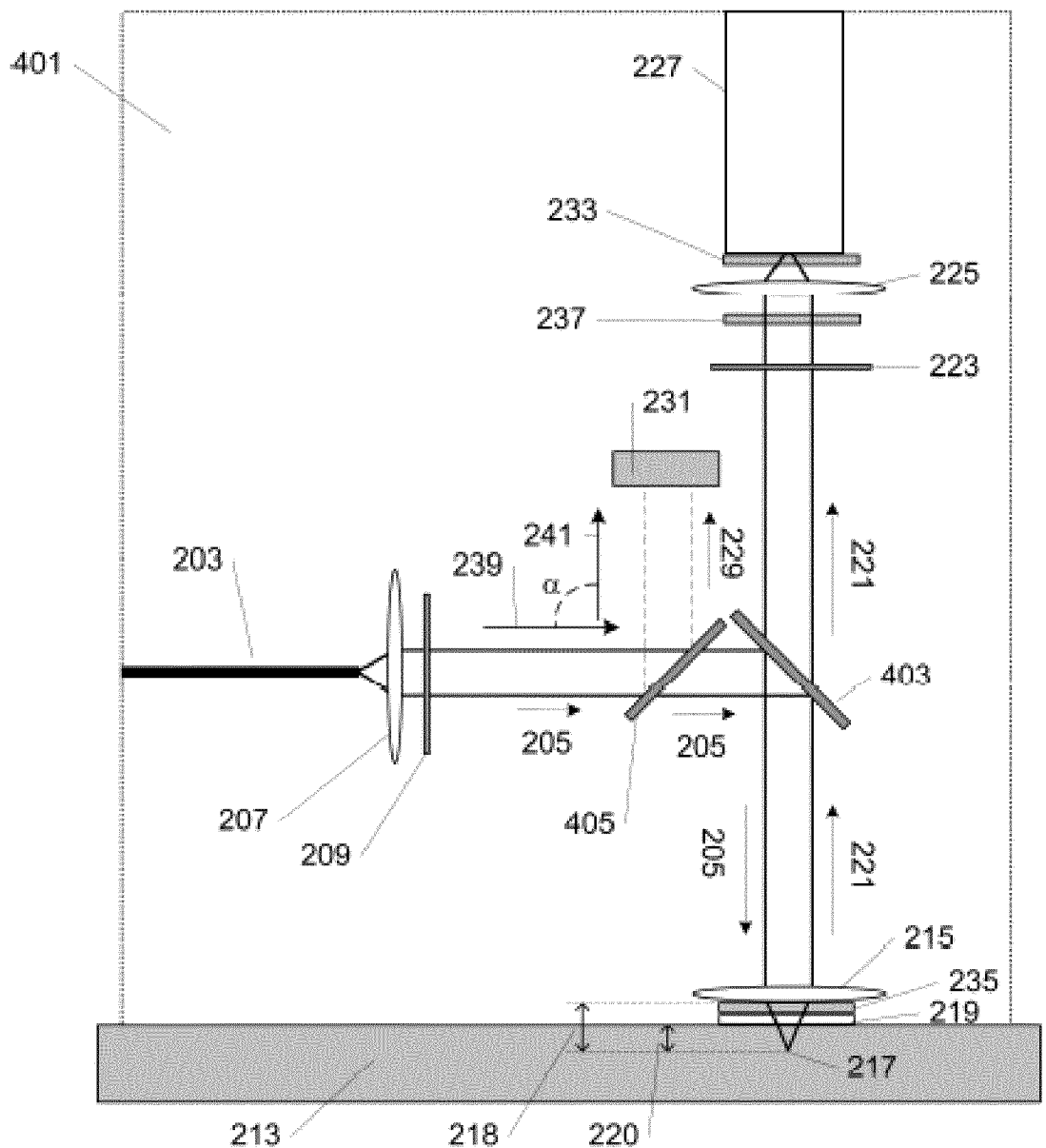
FIG. 4 shows a third embodiment of an optical probe forming part of the apparatus of FIG. 1.

FIG. 4 shows a third embodiment of the invention, where the optical probe 401 comprises an incoming light optical fibre 203 for guiding light into the optical probe 301, a first lens 207 for collimating the incoming light 205, a first filter 209 blocking any percentage between 0 and 100 of frequencies outside the frequency of the incoming light, a second lens 215 focusing the incoming light 205 into and for collecting the altered light 221 from the skin 213, a second filter 223 for optically filtrating the altered light 221, a third lens 225 for focusing the altered light 221 into a spectrophotometer 227, and a light logging device 231, which detects intensity variations in the incoming light.

As before, the fibre 203 and any further fibre that is present are preferably multimode mode fibers, but could also be single mode fibers. The two fibers 203 and 227 are normally arranged such that the direction of the light exiting the first fiber 203 and the direction of the light entering the spectrophotometer 227 are perpendicular in relation to one another. Alternative arrangements of the two fibers 203 and 227 and consequently the direction of the light exiting/entering them can also be found.

The two filters 209 and 223 are normally a band-pass filter, a notch filter, an edge filter or such. The second lens 215 is preferably convex, but could also be aspheric or planar.

The optical probe 401 further comprises a dichroic mirror 403 that either reflects or transmits any percentage between 0 and 100 of the light. The dichroic mirror 403 is in the current embodiment positioned at an angle of 45° in relation to the propagating direction of the incoming light 205, but could also be positioned at an angle between 0-90° as well.

According to the third embodiment of the invention, the dichroic mirror 403 reflects the majority of the incoming light 205 in a 90 degree angle onto the skin 213 and allows for the altered light 221 to pass through. In contrary to the first and the second embodiments, the smaller part 229 of the incoming light, which is used for light logging, is not collected after passing through or being reflected by the dichroic mirror 403. Instead, an optical splitting device 405 positioned between the first filter 209 and the dichroic mirror 403 is employed to direct a smaller fraction 229 of the incoming light onto the light logging device 231. The splitting device 405 can be a beam splitter, a dichroic mirror allowing most of the incoming light to pass through, a low density filter or similar.

In one embodiment of the invention, the percent of the incoming light 205 which is reflected and transmitted by the dichroic mirror 403 is re_in≥90% of (re_in+tr_in) and tr_in≤10% of (re_in+tr_in), respectively, and the percent of the altered light 221 which is reflected and transmitted by the dichroic mirror 403 is re_se≤10% of (re_se+tr_se) and tr_se≥90% of (re_se+tr_se), respectively.

The optical probe 401 may further optionally comprises a thin window 219, which is positioned between the second lens 215 and the skin 213, a first optical aperture 233, second aperture 235 normally positioned between the second lens 215 and the skin 213, and a third aperture 237 normally be positioned just before the third lens 225. According to this second embodiment of the invention, the apertures 233 and 235 are each formed as a separate element. However, a narrow opening of a second fiber communicating with the spectrophotometer 227 can equally well function as a first aperture 233 and a narrow opening of the optical probe 201 at the point where light exits/is collected by the second lens 215 can equally well function as a first aperture 233.

Typical sample penetration depths 220 are in the rage between 150-500 µm depending on the focal length 218 of the second lens 215 and the thickness of the window 219, if such is part of the optical probe 401. Both shorter and longer penetrations depths 220 can also be obtained.

The advantages with the optical probe 401 are the same as the ones described in relation to the optical probe 201 shown in FIG. 2.

The optical probes 201, 301, and 401 are all constructed such that the optical elements inside are positioned in very close proximity to one another, and the FIGS. 2-4 are only meant as illustrations and do not show the accurate distances between the different optical elements.

An advantage of placing the optical elements inside the optical probe in as close proximity as possible, is that this feature enhances both the intensity of the incoming light at the sample focus point and the efficiency by which the altered light is collected, since effects from diffraction of the incoming light and/or the altered light is diminished.

EXAMPLES

Apparatus generally as described above with reference to FIG. 2, but omitting the window 235, was set to focus its output of light to a depth of approximately 250 µm beyond the lower face of the objective lens 215 which was brought directly into contact with the finger pad skin of a series of volunteers.

A Raman spectrum was obtained from each patient. Sample results are shown in FIG. 7. It was noted whether a meaningful glucose concentration measurement could be obtained from each patient. In one case (patient 127) it was noted that the stratum corneum was too thick for this to be possible. It can be seen in FIG. 7 that the relative heights of the peaks at 883/4 $cm^{-1}$ and 893/4/5/6 $cm^{-1}$ are reversed compared to the other patients, with the collagen type I peak at 883/4 cm-1 being smaller than the adjacent 893/5/6 $cm^{-1}$ phosphodiester, deoxyribose peak. This is due to the differing abundances of collagen type I and DNA above and below the floor of the stratum corneum. An 883/4 $cm^{-1}$ peak relatively somewhat less high or more preferably higher than the 893-6 $cm^{-1}$ peak is consistent with a situation such that the collected signal originates from the part of the skin below stratum corneum. An 893-6 $cm^{-1}$ peak only slightly less high or even relatively higher than 883/4 $cm^{-1}$ peak is an outlier having a thicker than usual stratum corneum and indicates that the signal originates from within the stratum corneum.

Relatively high peaks at 1445 cm-1 and 1650 cm-1 also indicates an outlier that is to say a patient with a thick stratum corneum, leading to the signal probably deriving from within the stratum corneum.

By detecting the relative height of these peaks the apparatus was able to provide an output indicating whether the stratum corneum of each patient was sufficiently thin for a good glucose reading to be obtained.

As a further safeguard, when the ratio of the 883/4 $cm^{-1}$ and 893-896 $cm^{-1}$ peaks is above a selected threshold, so that the situation is consistent with the signals arising from below the stratum corneum, one may choose to view such a situation as doubtful if at the same time the peaks at 1445 cm-1 and 1650 cm-1 are relatively large compared to their mean size in a statistically relevant sample of such measurements at other sites and in other persons.

Figure 12:
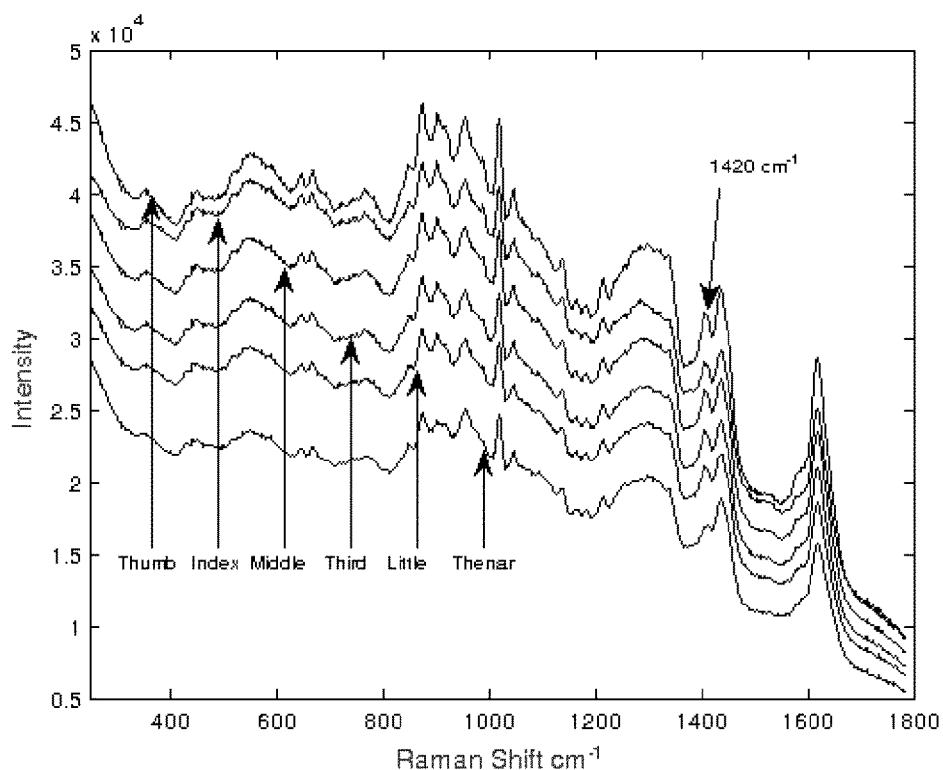
FIG. 12 shows Raman spectra obtained using apparatus set to a very short focal depth of 160 µm in air measured at different finger pad locations and at the thenar.

FIG. 12 shows Raman spectra obtained using apparatus set to a very short focal depth of 160 µm in air, which is too short for making glucose measurements in skin. The separate spectra in FIG. 12 were obtained from finger pads of each finger and the thumb and also from the thenar. The stratum corneum will be thickest in the thumb and thinnest in the thenar. It is observable that a peak at 1420 $cm^{-1}$ is largest in the thumb and smallest in the thenar spectrum. This peak may originate from 2-deoxyribose, a component of DNA. As the spectra originate from an upper part of the stratum corneum, because of the short focus used, these findings may indicate a higher concentration of DNA in the upper layers of the stratum corneum. This might be due to a lower water content.

A relatively large peak at this location may also be taken as an indication that the Raman spectrum is being obtained from too shallow a depth below the skin surface, indicating a need to readjust the apparatus. In particular, if the peak at 1420 $cm^{-1}$ is larger than ⅓ of the size of the peak at 1445 $cm^{-1}$ then the system should be regarded as not suitably set for reliable concentration measurements and the depth of the focusing of the light and the depth from which Raman signals are gathered needs to be increased.

REFERENCE NUMERAL LIST

101: Optical probe
103: Light source, e.g. a laser
105: incoming light optical fibre
107: Sample, i.e. a patients arm
109: Electrical signal connection
111: Computer
201: Optical probe according to the first embodiment
203: Incoming light optical fiber
205: Incoming light
207: First lens
209: First filter
211: Dichroic mirror
213: Skin
215: Second lens
217: Focus point
218: Focal length of the first lens
219: Window
220: Penetration depth
221: Altered light
223: Second filter
225: Third lens 227: Spectrophotometer
229: Minor part of the incoming light used for light logging
231: Light logging device
233: First aperture
235: Second aperture
237: Third aperture
301: Optical probe according to the second embodiment
303: Dichroic mirror
401: Optical probe according to the third embodiment
403: Dichroic mirror
405: Optical splitting device
510 compound lens first element
512 compound lens second element
514 lens housing first section
516 lens housing second section
518 piezoelectric ring element
520 threaded cylinder
522 annular head
524 variable gap In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A method for predicting whether a spectrum of Raman signals received transdermally in a confocal detector apparatus and having at least one component expected to have an intensity representing the concentration of a skin component at a point of origin of said Raman signals below the surface of the skin will accurately represent said concentration, which method comprises the steps of:
   analysing features of said spectrum relating to skin components other than the skin component the concentration of which is to be measured, and thereby determining whether the Raman signals originate primarily within the stratum corneum so that the spectrum will be less likely to represent said concentration accurately and if it is determined that Raman signals do not originate primarily within the stratum corneum and do originate primarily below the stratum corneum, determining that the spectrum will be more likely to represent said concentration accurately.

2. A method as claimed in claim 1, which method comprises analysing said signals to compare the relative intensities of Raman signals originating from a first skin component and Raman signals originating from a second skin component, wherein said relative intensities are indicative of whether the Raman signals originate primarily within the stratum corneum or primarily below the stratum corneum.

3. A method as claimed in claim 2, wherein said first skin component produces a peak in the Raman spectrum at 883-884 $cm^{-1}$.

4. A method as claimed in claim 2, wherein said second skin component produces a peak in the Raman spectrum at 893-896 $cm^{-1}$.

5. A method as claimed in claim 2, wherein said first skin component is collagen type I.

6. A method as claimed in claim 2, wherein said second skin component is DNA and the respective signal arises from phosphodiester bonds thereof.

7. A method as claimed in claim 2, wherein said first skin component produces a first peak in the Raman spectrum at 883-884 $cm^{-1}$ and wherein said second skin component produces a second peak in the Raman spectrum at 893-896 $cm^{-1}$.

8. A method as claimed in claim 7, further comprising the step of comparing the intensities of said first and second peaks and producing an output indicative that the signals arise from below the stratum corneum if the size of said first peak divided by the size of said second peak is more than a selected value R.

9. A method as claimed in claim 8, wherein R is selected to be 0.75, preferably 0.95 and more preferably 1.0.

10. A method as claimed in claim 2, wherein if the comparison of the relative intensities of Raman signals originating from a first skin component and Raman signals originating from a second skin component is indicative that the Raman signals originate primarily below the stratum corneum, said method further comprises determining whether the size of a further peak in the spectrum associated with a skin component prevalent in the stratum corneum is more than y standard deviations greater than a mean value for the size of that peak in a statistically valid sample of similar spectra, a positive determination indicating a probability that the Raman signals do not after all originate primarily below the stratum corneum, wherein y is a preselected value in the range of from 0.5 to 2.

11. A method as claimed in claim 1, further comprising adjusting said transdermally operating confocal detector apparatus in response to a finding that the Raman signals originate primarily from within the stratum corneum, said adjustment altering the depth of origin of said Raman signals such that the depth is no longer determined to be within the stratum corneum.

12. A method as claimed in claim 11, wherein said transdermally operating confocal detector apparatus comprises an objective lens having a focal length and said method of altering the depth of origin of the Raman signals comprises altering the focal length of the objective lens by replacement of the objective lens or by adjustment of the objective lens.

13. A method as claimed in claim 12, wherein said transdermally operating confocal detector apparatus comprises a compound objective lens comprising at least a first element and a second element spaced from the first element, and said method of altering the depth of origin of the Raman signals comprises altering the spacing of two or more elements to adjust the focal length of the compound objective lens.

14. A method as claimed in claim 1, wherein the method is arranged to determine whether or not the signal originates within the stratum corneum irrespective of whether the signal originates within any other layer in the epidermis.

15. Transdermally operating confocal detector apparatus for non-invasive in vivo measurement by Raman spectroscopy of the concentration of a skin component present in the skin of a subject, comprising:
   a light source,
   optical components defining a light path from said light source to a measurement location,
   a spectrum analysis unit,
   optical components defining a return path for Raman scattered light from said measurement location to said spectrum analysis unit, wherein said spectrum analysis unit is arranged and configured to operate to determine whether the origin of Raman signals received therein lies within the stratum corneum or below it by analysing features of Raman scattered light relating to skin components other than the skin component the concentration of which is to be measured and thereby determining whether the Raman signals originate primarily within the stratum corneum or primarily below the stratum corneum, and if it is determined that the Raman signals do not originate primarily within the stratum corneum and do originate primarily below the stratum corneum, determining that the spectrum will be more likely to represent said concentration accurately.

16. Apparatus as claimed in claim 15, wherein said spectrum analysis unit operates by analysing said signals to compare the relative intensities of Raman signals originating from a first skin component and Raman signals originating from a second skin component, wherein said relative intensities are indicative of whether the Raman signals originate primarily within the stratum corneum or primarily below the stratum corneum.

17. Apparatus as claimed in claim 16, wherein said spectrum analysis unit determines the size of a peak in the Raman spectrum at 883-884 $cm^{-1}$ produced by said first skin component.

18. Apparatus as claimed in claim 16, wherein said spectrum analysis unit determines the size of a peak in the Raman spectrum at 893-896 $cm^{-1}$ produced by said second skin component.

19. Apparatus as claimed in claim 16, wherein said spectrum analysis unit determines a ratio between the size of a first peak in the Raman spectrum at 883-884 $cm^{-1}$ and the size of a second peak in the Raman spectrum at 893-896 $cm^{-1}$.

20. Apparatus as claimed in claim 19, wherein said spectrum analysis unit produces an output indicative that the signals arise from below the stratum corneum if the size of said first peak divided by the size of said second peak is more than a selected value R.

21. Apparatus as claimed in claim 20, wherein R is pre-set to be 0.75, preferably 0.95 and more preferably 1.0.

22. Apparatus as claimed in claim 16, wherein if the signal analysis unit determines that comparison of the relative intensities of Raman signals originating from a first skin component and Raman signals originating from a second skin component is indicative that the Raman signals originate primarily below the stratum corneum, said signal analysis unit further determines whether the size of a further peak in the spectrum associated with a skin component prevalent in the stratum corneum is more than y standard deviations greater than a mean value for the size of that peak in a statistically valid sample of similar spectra, a positive determination indicating a probability that the Raman signals do not after all originate primarily below the stratum corneum, wherein y is a preselected value in the range of from 0.5 to 2.

23. Apparatus method as claimed in claim 15, wherein said transdermally operating confocal detector apparatus comprises an objective lens having an adjustable focal length.

24. Apparatus as claimed in claim 23, wherein said objective lens is a compound objective lens comprising at least a first element and a second element spaced from the first element, and said lens is adjustable by altering the spacing of two or more elements to adjust the focal length of the compound objective lens.

25. Apparatus as claimed in claim 15, wherein the apparatus is arranged and configured to determine whether or not the signal originates within the stratum corneum irrespective of whether it originates within any other layer in the epidermis.

* * * * *